(12) United States Patent
Mottola et al.

(10) Patent No.: US 9,561,327 B2
(45) Date of Patent: Feb. 7, 2017

(54) LOCKABLE SYRINGE ASSEMBLIES AND RELATED DEVICES AND METHODS

(71) Applicant: Merit Medical Systems, Inc., South Jordan, UT (US)

(72) Inventors: Jim Mottola, Salt Lake City, UT (US); Darla Gill, Salt Lake City, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/212,096

(22) Filed: Mar. 14, 2014

(65) Prior Publication Data

US 2014/0276592 A1  Sep. 18, 2014

Related U.S. Application Data

(60) Provisional application No. 61/799,133, filed on Mar. 15, 2013.

(51) Int. Cl.
 *A61M 5/315* (2006.01)
 *A61B 5/15* (2006.01)
 (Continued)

(52) U.S. Cl.
 CPC .......... *A61M 5/31505* (2013.01); *A61B 5/153* (2013.01); *A61B 5/15003* (2013.01);
 (Continued)

(58) Field of Classification Search
 CPC  A61M 5/315; A61M 5/31505; A61M 5/3135; A61M 39/22; A61M 5/31501; A61B 5/1433;A61B 5/153; A61B 5/150259; A61B 5/150236; A61B 5/150244; A61B 5/15026
 (Continued)

(56) References Cited

U.S. PATENT DOCUMENTS

| 913,297 A | 2/1909 | Krautschneider |
|---|---|---|
| 1,393,720 A | 10/1921 | Lomas et al. |

(Continued)

FOREIGN PATENT DOCUMENTS

| EP | 0208975 | 1/1987 |
|---|---|---|
| EP | 0420126 | 9/1990 |

(Continued)

OTHER PUBLICATIONS

International Search Report and Written Opinion dated Aug. 21, 2014 for PCT/US2014/027649.

(Continued)

*Primary Examiner* — Kevin C Sirmons
*Assistant Examiner* — Tiffany Legette
(74) *Attorney, Agent, or Firm* — Stoel Rives LLP

(57) ABSTRACT

The embodiments disclosed herein relate to lockable syringe assemblies and related devices and methods. The syringe assembly may include a barrel, a plunger, and a locking mechanism. In some arrangements, the locking mechanism is an elastomeric locking ring or a rigid partial ring. The plunger may include a plurality of ribs and is longitudinally moveable within the barrel. Once the plunger is disposed at a desired longitudinal location, the plunger can be axially rotated and locked in such a way that further longitudinal movement is restricted.

16 Claims, 14 Drawing Sheets

(51) Int. Cl.
*A61B 5/153* (2006.01)
*A61M 5/31* (2006.01)

(52) U.S. Cl.
CPC .. *A61B 5/150236* (2013.01); *A61B 5/150244* (2013.01); *A61B 5/150259* (2013.01); *A61B 5/150992* (2013.01); *A61M 5/3135* (2013.01)

(58) Field of Classification Search
USPC .................................. 604/208, 220, 506, 218
See application file for complete search history.

(56) References Cited

U.S. PATENT DOCUMENTS

| | | | |
|---|---|---|---|
| 3,831,603 A | | 8/1974 | Armenti |
| 3,938,505 A | | 2/1976 | Jamshidi |
| 4,275,729 A | | 6/1981 | Silver et al. |
| 4,386,606 A | | 6/1983 | Tretinyak |
| 4,562,844 A | | 1/1986 | Carpenter |
| 4,635,792 A | | 1/1987 | Yamada et al. |
| 4,711,637 A | | 12/1987 | Leigh et al. |
| 4,747,484 A | | 5/1988 | Ackeret |
| 4,758,232 A | * | 7/1988 | Chak ........................... 604/220 |
| 4,807,749 A | | 2/1989 | Ackeret |
| 4,810,249 A | | 3/1989 | Haber et al. |
| 4,875,578 A | | 10/1989 | Nehl |
| 5,000,735 A | * | 3/1991 | Whelan .................. A61M 5/50 604/110 |
| 5,011,010 A | | 4/1991 | Francis et al. |
| 5,049,135 A | | 9/1991 | Davis |
| 5,135,111 A | | 8/1992 | Stoger |
| 5,213,209 A | | 5/1993 | Song |
| 5,306,248 A | | 4/1994 | Barrington |
| 5,306,258 A | | 4/1994 | de la Fuente |
| 5,358,497 A | * | 10/1994 | Dorsey ................. A61M 5/315 604/220 |
| 5,413,115 A | | 5/1995 | Baldwin |
| 5,685,864 A | | 11/1997 | Shanley et al. |
| 2004/0236283 A1 | | 11/2004 | Tang |
| 2006/0264837 A1 | * | 11/2006 | Bloom et al. ................. 604/208 |
| 2009/0247961 A1 | * | 10/2009 | Carlyon .................. A61M 5/28 604/237 |
| 2009/0326479 A1 | * | 12/2009 | Janish ................ A61M 5/31511 604/218 |
| 2011/0009829 A1 | | 1/2011 | Kosinski et al. |
| 2011/0319864 A1 | * | 12/2011 | Beller ................. A61M 5/2033 604/506 |

FOREIGN PATENT DOCUMENTS

| | | |
|---|---|---|
| WO | WO94/09838 | 5/1994 |
| WO | 2011006086 | 1/2011 |
| WO | 2011006103 | 1/2011 |

OTHER PUBLICATIONS

International Preliminary Report dated Sep. 24, 2015 for PCT/US2014/027649.
European Search Report dated Sep. 19, 2016 for EP14771008.1.

\* cited by examiner

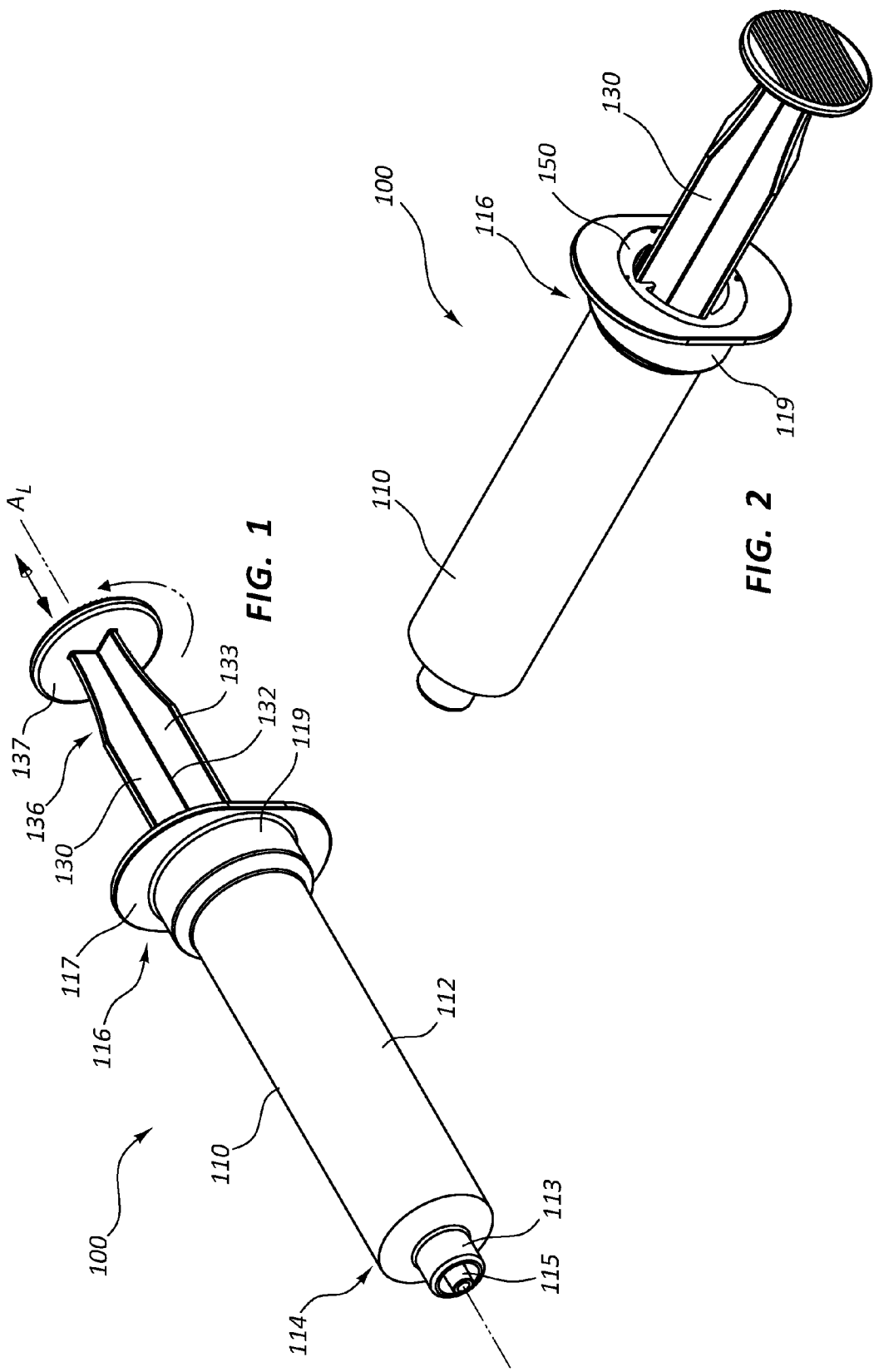

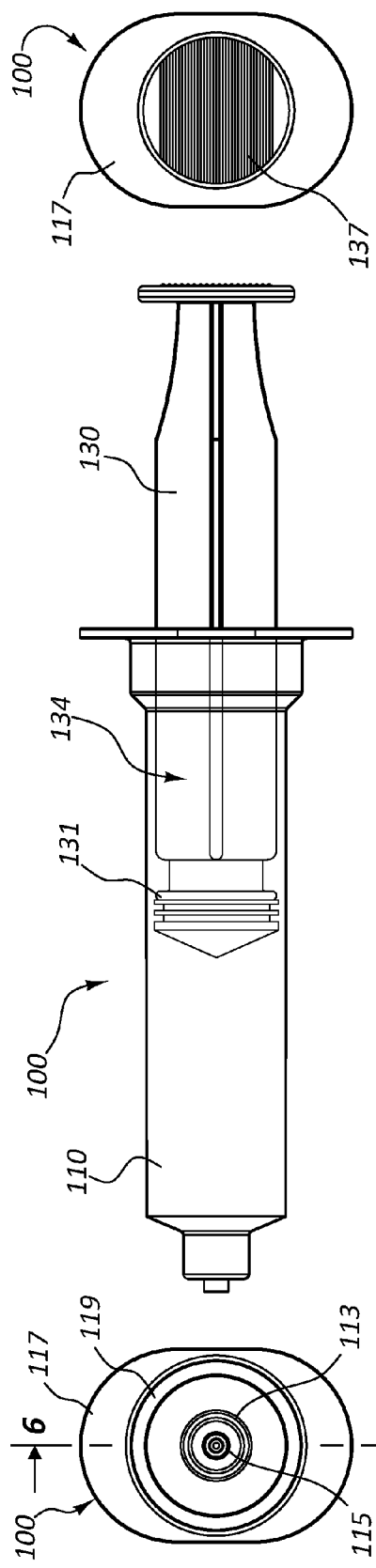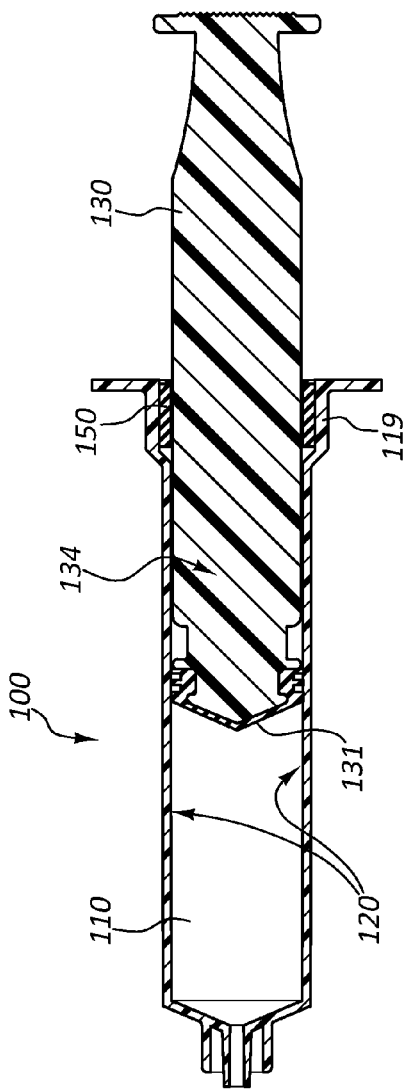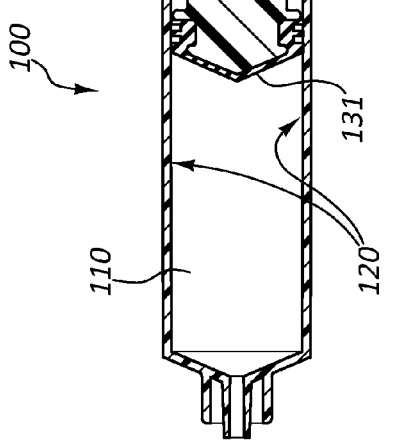

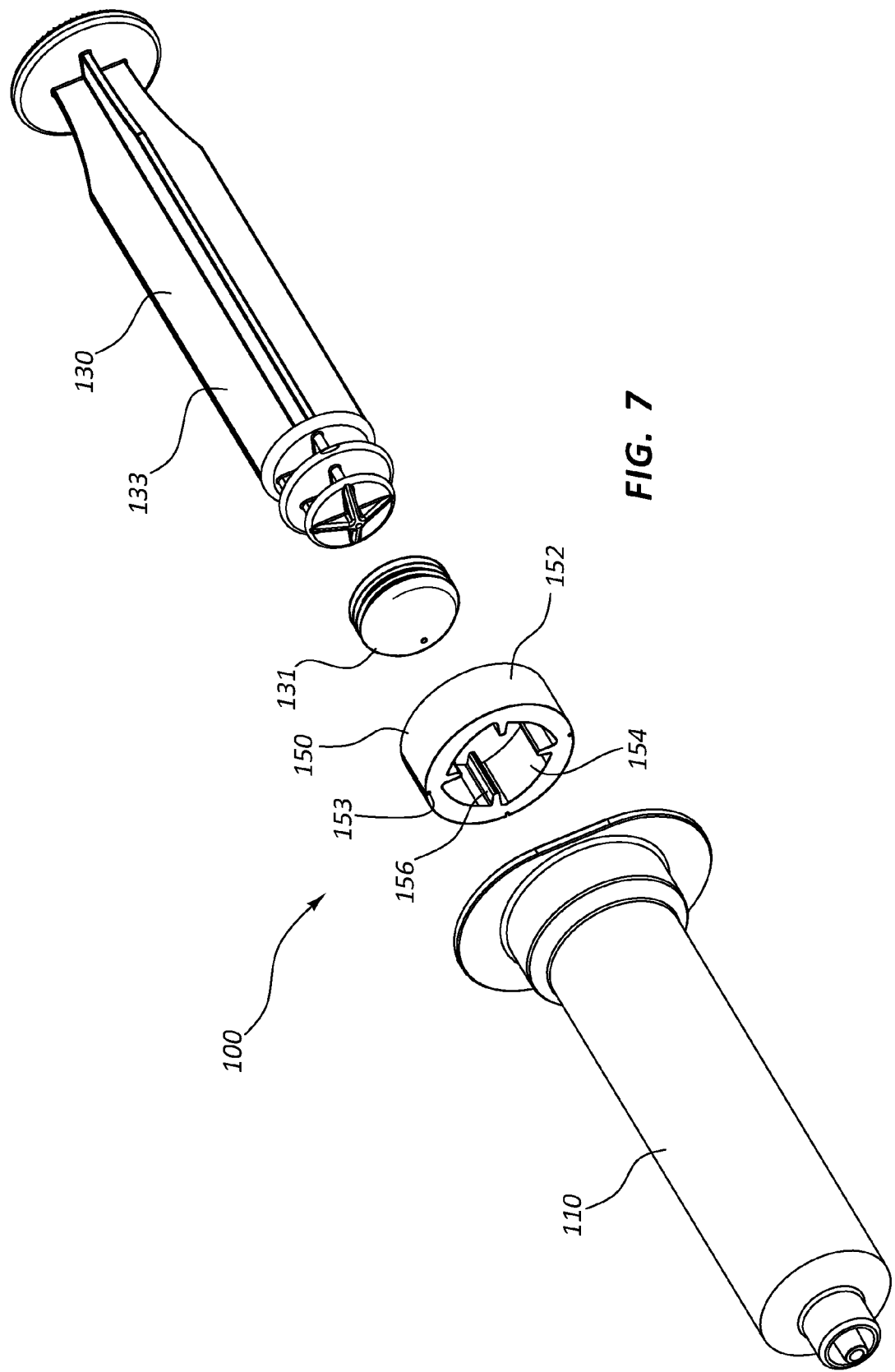

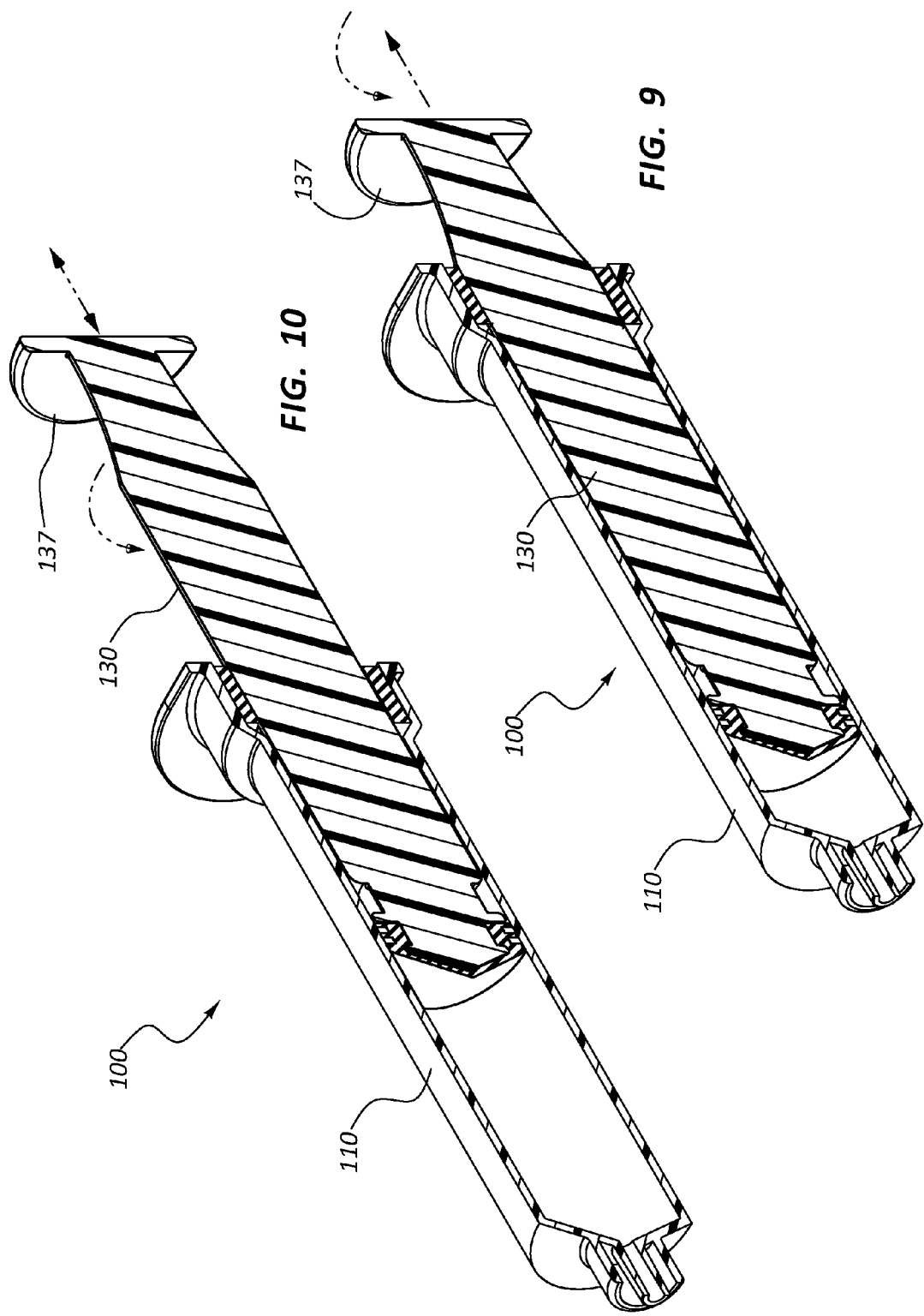

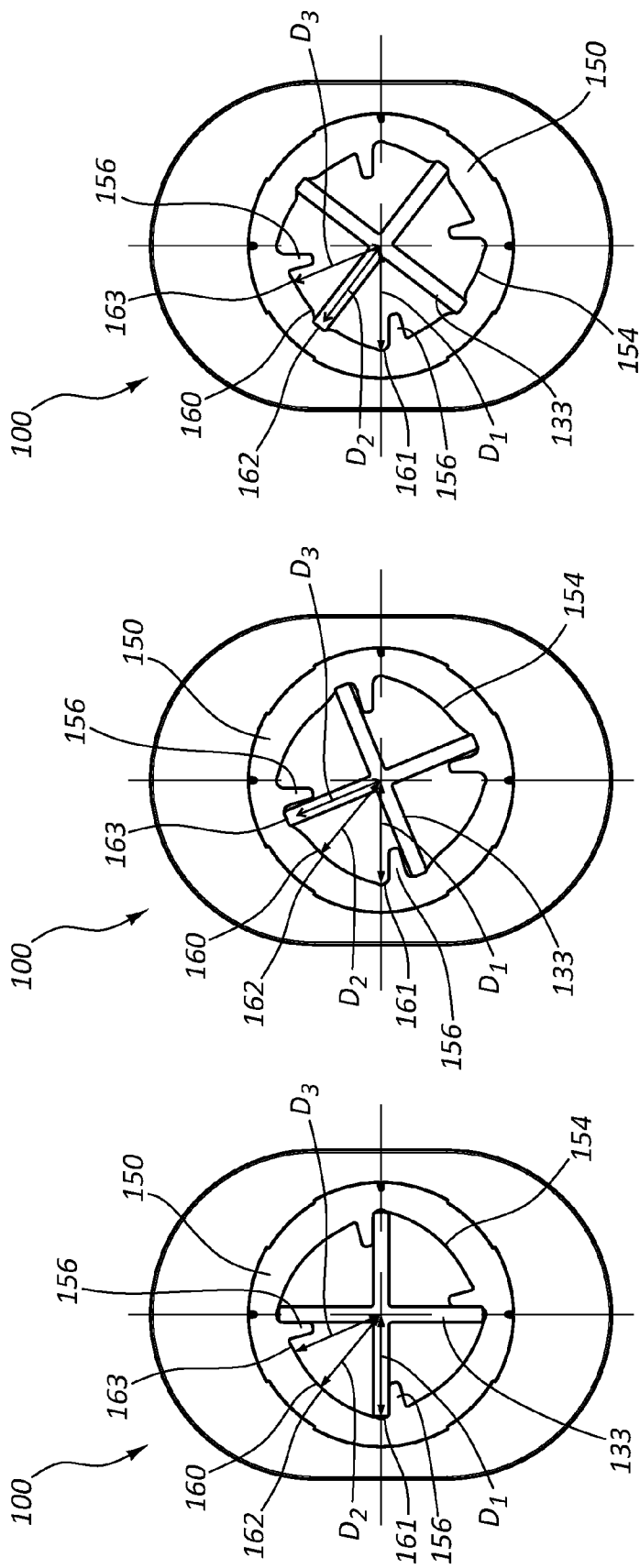

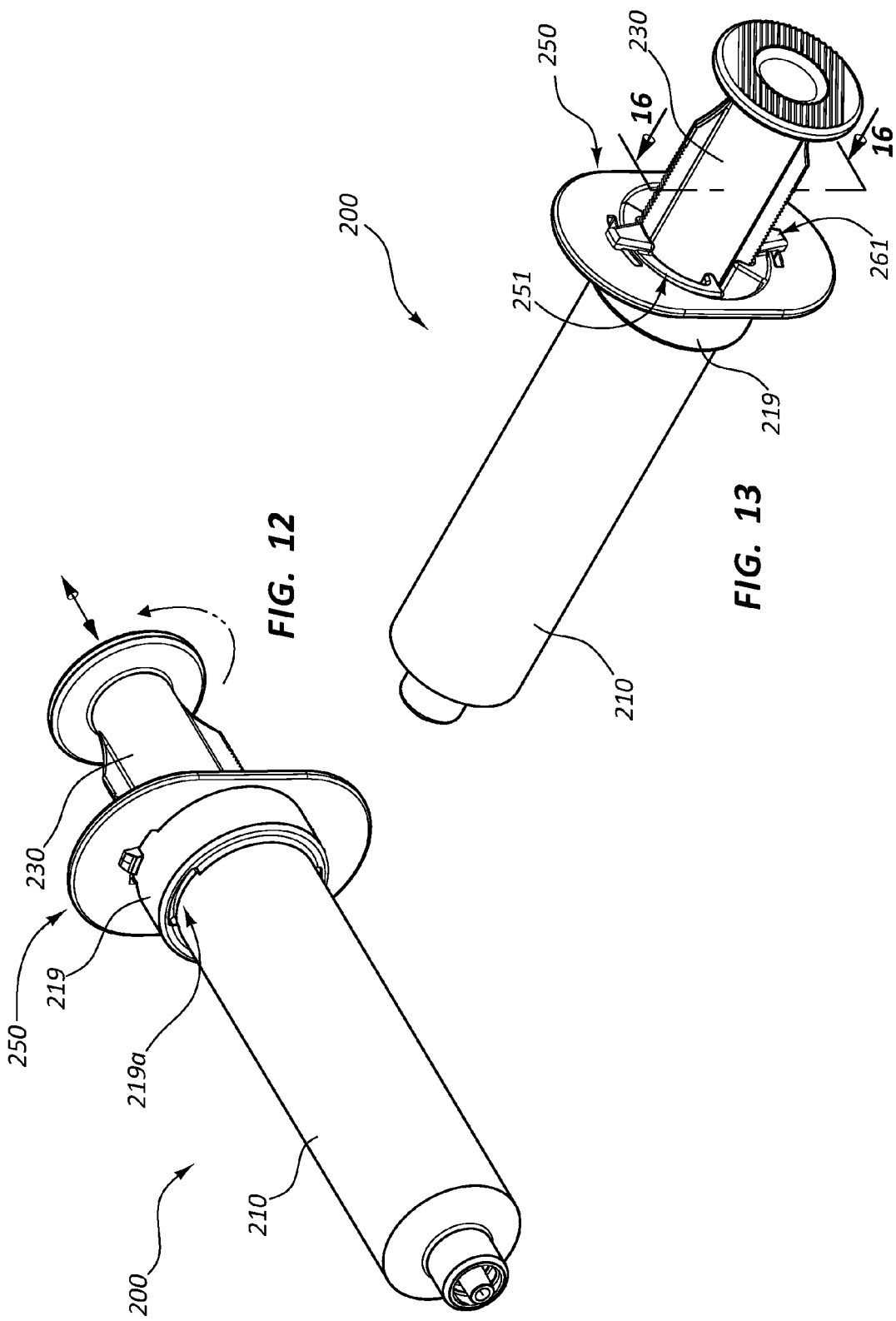

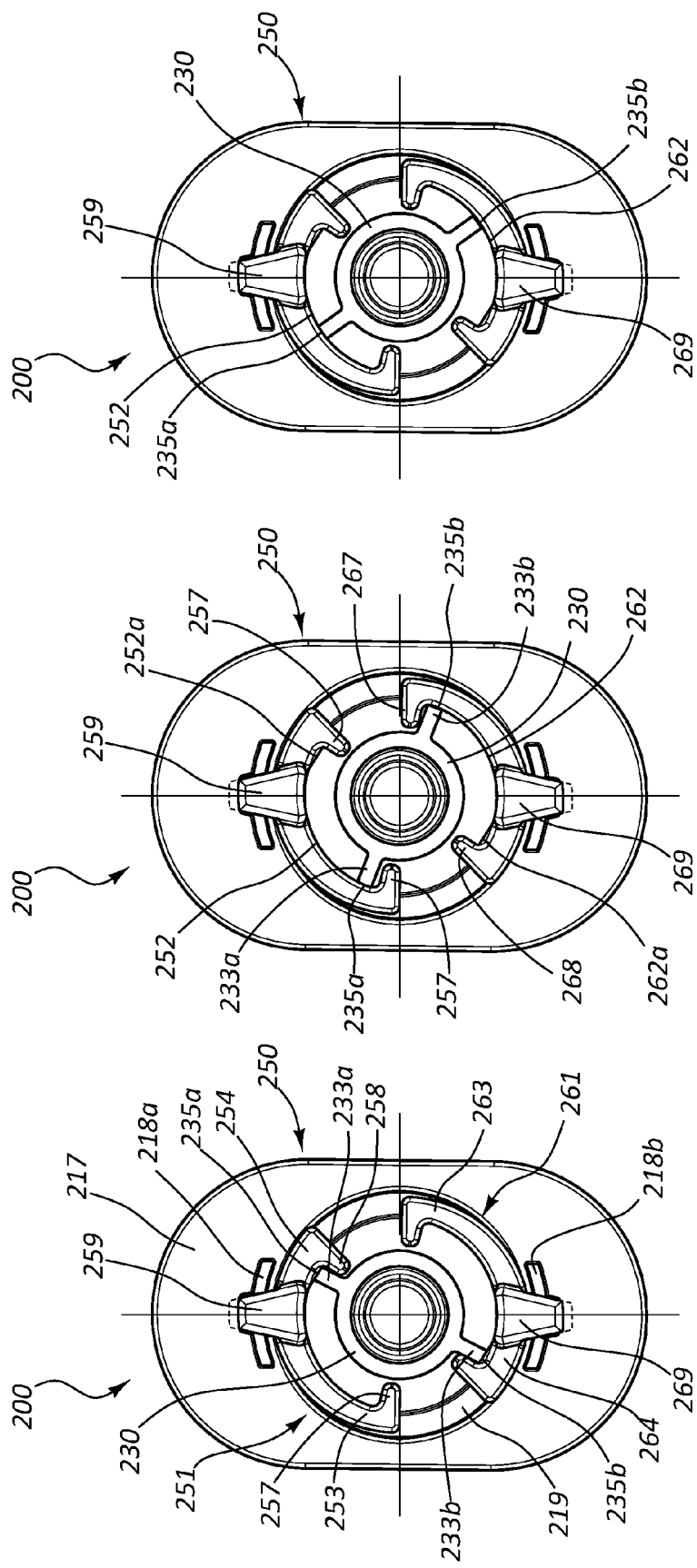

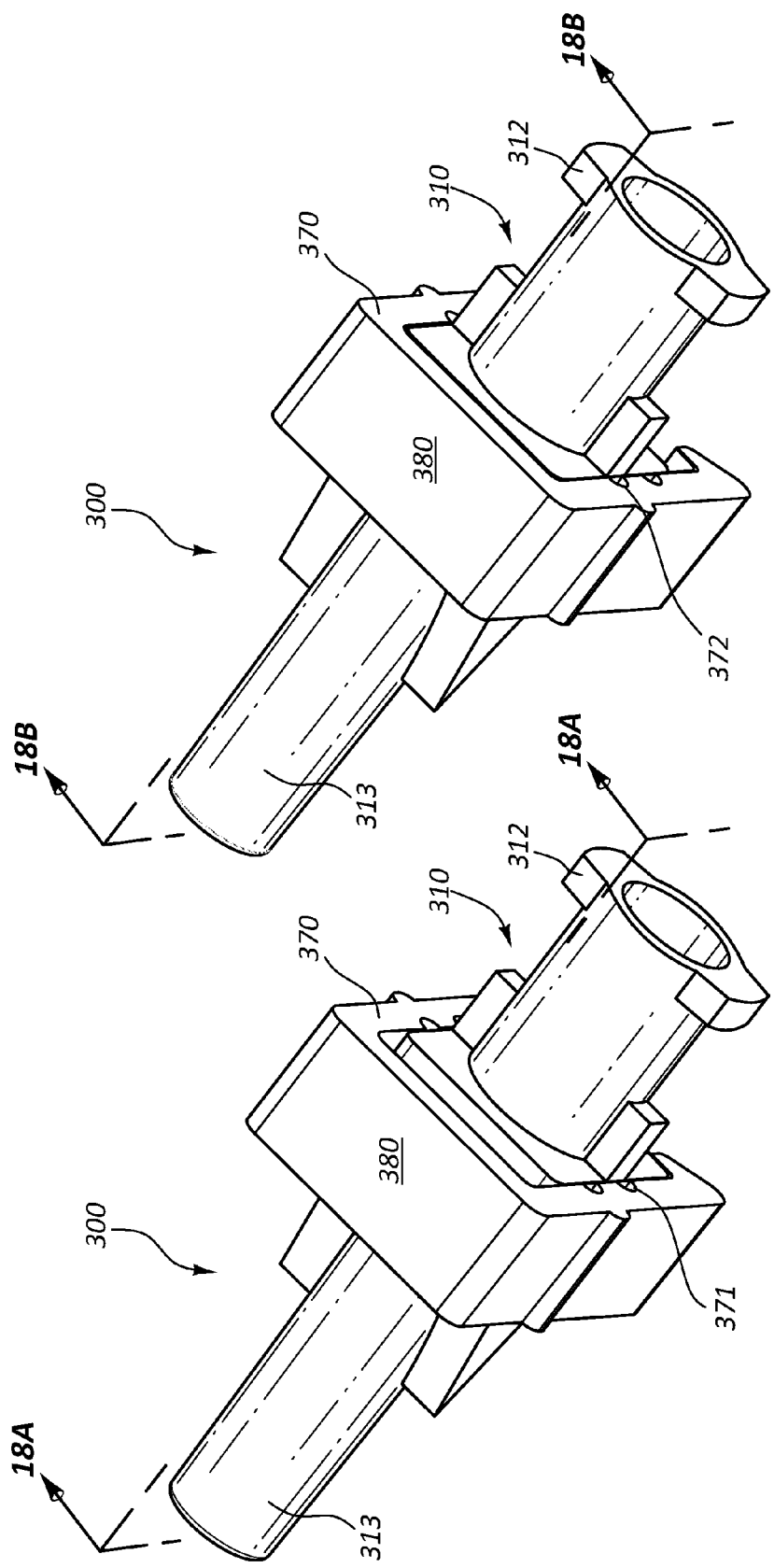

LOCKABLE SYRINGE ASSEMBLIES AND RELATED DEVICES AND METHODS

CROSS-REFERENCE TO RELATED APPLICATIONS

Under 35 U.S.C. §119(e), this application claims the benefit of U.S. Provisional Patent Application No. 61/799,133, entitled "LOCKABLE SYRINGE ASSEMBLY," filed Mar. 15, 2013, the contents of which are hereby incorporated herein by reference in their entirety.

TECHNICAL FIELD

The present disclosure relates generally to syringe assemblies and related devices and methods. More particularly, the present disclosure relates to syringe assemblies wherein the plunger is lockable at a position within the syringe barrel and to devices and methods related to the syringe assemblies.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1 is a perspective view of one embodiment of a syringe assembly.

FIG. 2 is another perspective view of the syringe assembly of FIG. 1.

FIG. 3 is a side view of the syringe assembly of FIG. 1.

FIG. 4 is an end view of the syringe assembly of FIG. 1.

FIG. 5 is another end view of the syringe assembly of FIG. 1.

FIG. 6 is a cross-sectional view of the syringe assembly of FIG. 1, taken along the view line 6-6 of FIG. 4.

FIG. 7 is an exploded view of the syringe assembly of FIG. 1.

FIG. 9 is a cross-sectional view of the syringe assembly of FIG. 1, also taken along the view line 6-6.

FIG. 10 is another cross-sectional view of the syringe assembly of FIG. 1, also taken along the view line 6-6.

FIGS. 11A-11C are cross-sectional views of the syringe assembly of FIG. 1, taken along the view line 11-11, showing various configurations of a locking mechanism.

FIG. 12 is a perspective view of another embodiment of a syringe assembly.

FIG. 13 is another perspective view of the syringe assembly of FIG. 12.

FIGS. 16A-16C are cross-sectional views of the syringe assembly of FIG. 12, taken along the view line 16-16, showing various configurations of a locking mechanism.

FIG. 17C is an assembled view of the valve of FIG. 17A in a first position.

FIG. 17D is an assembled view of the valve of FIG. 17A in a second position.

DETAILED DESCRIPTION

Figure 8:
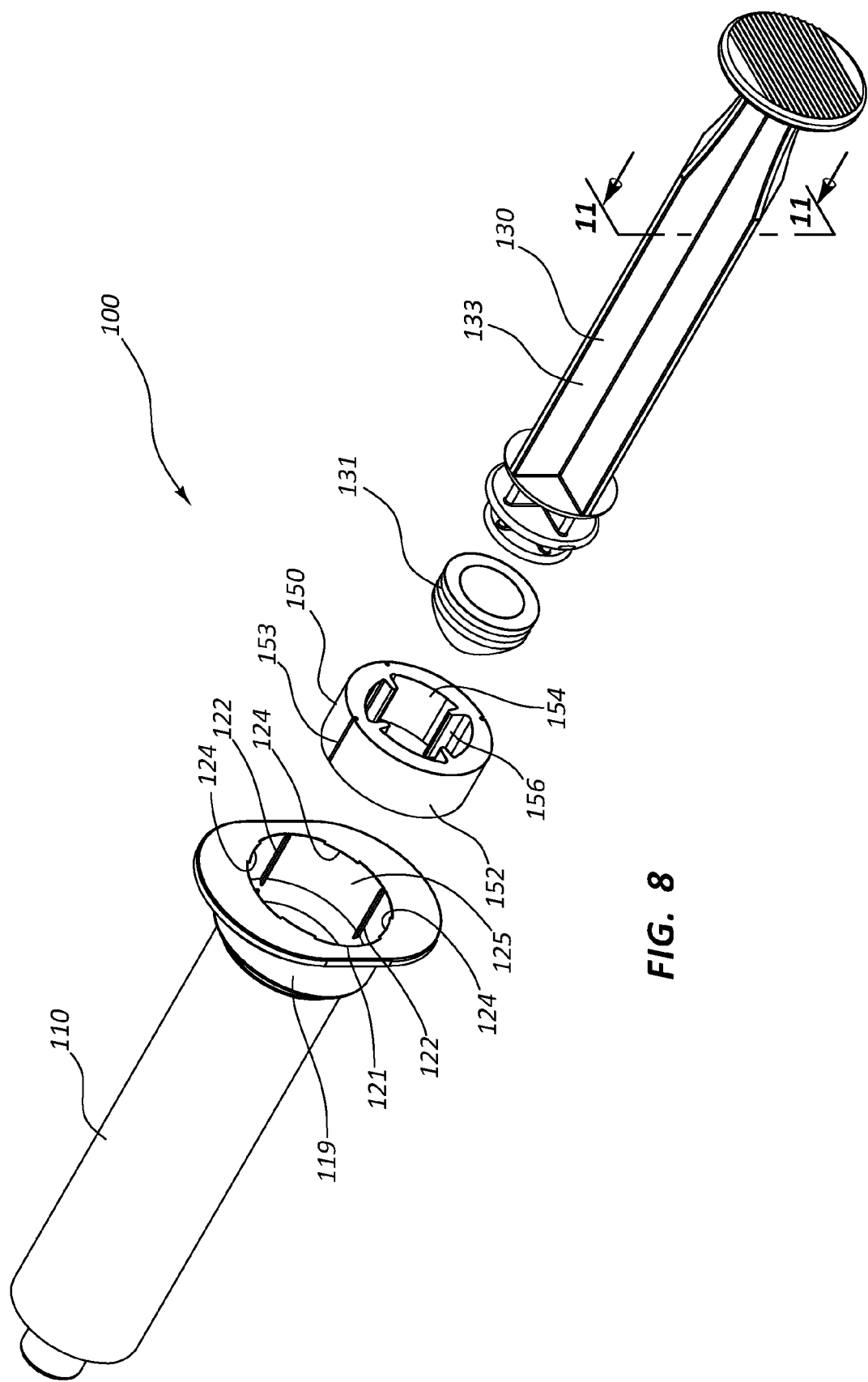
FIG. 8 is another exploded view of the syringe assembly of FIG. 1.

The various embodiments disclosed herein relate to a syringe assembly. More particularly, the embodiments relate to a lockable syringe assembly wherein the plunger is lockable at a desired longitudinal position within the syringe barrel. Lockable syringe assemblies may be used in many medical applications. For example, lockable syringe assemblies may be useful for withdrawing fluids from within a patient. A practitioner may withdraw the plunger from the syringe assembly, thereby creating a negative gauge pressure or vacuum inside the syringe barrel. The practitioner may then lock the plunger at a desired location within the syringe barrel to maintain the negative gauge pressure, facilitating withdrawal of fluid from within the patient.

Embodiments may be best understood by reference to the drawings, wherein like parts are designated by like numerals throughout. It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, as claimed, but is merely representative of various embodiments. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component. The terms "abut" and "abutting" refer to items that are in direct physical contact with each other, although the items may not necessarily be attached.

The terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to a syringe assembly, the distal end of the syringe assembly refers to the end nearest the inlet/outlet port of the syringe and the proximal end refers to the opposite end, the end nearest the gripping member. Further, it will be appreciated that the phrase "distal end" always refers to the end nearest the inlet/outlet port, even if the distal end is temporarily closer to the practitioner at one or more points in a procedure.

FIG. 1 is a perspective view of one embodiment of a syringe assembly, a syringe assembly 100. As shown in FIG. 1, the syringe assembly 100 may comprise a barrel 110 and a plunger 130. Although not depicted in FIG. 1, the syringe assembly 100 further comprises a locking mechanism.

When engaged, the locking mechanism is configured to restrict longitudinal movement of the plunger 130 within the barrel 110.

The barrel 110 is hollow or substantially hollow. In some embodiments, the barrel 110 comprises an elongated cylindrical tube 112 having a lumen extending therethrough. The barrel 110 comprises a distal end 114 and a proximal end 116. The distal end 114 of the barrel 110 may comprise an opening 115. In some embodiments, the opening 115 is described as an inlet/outlet port. The opening 115 may be configured to allow passage of fluids, such as liquids and gases, into and out of the barrel 110. The distal end 114 of the barrel 110 may also be configured to couple to a needle or other auxiliary device, which can facilitate access into a human body for the introduction or removal of fluids. For example, the distal end 114 of the barrel 110 may comprise a fitting 113, such as a luer fitting. The luer fitting may be threaded. Other types of known fittings 113 may also be used.

The proximal end 116 of the barrel 110 comprises an opening through which the plunger 130 extends and/or is inserted. The proximal end 116 of the barrel 110 may also comprise one or more gripping members 117. The one or more gripping members 117 extend outwardly from the barrel 110 and facilitate use of the syringe assembly 100 by a practitioner. In some embodiments, the one or more gripping members 117 comprise finger grips. In other embodiments, the one or more gripping members 117 comprise handles or like structures.

In some embodiments, a locking mechanism is disposed within the barrel 110. As shown in FIG. 1, for example, the barrel 110 comprises a seating region 119. The inner and outer diameters of the seating region 119 may be greater than the respective inner and outer diameters of the remainder of the barrel 110. The seating region 119 can be disposed at or near the proximal end 116 of the barrel 110. Alternatively, the seating region 119 is disposed at other locations within or adjacent to the barrel 110.

The seating region 119 may be couple to and/or retain the locking mechanism in a substantially fixed position. For example, the inner surface of the seating region 119 may comprise one or more protrusions that are configured to engage with the locking mechanism. One or more retaining ridges can also be used to retain the locking mechanism.

In some embodiments, the locking mechanism is operably coupled to the barrel 110 and the plunger 130. The locking mechanism may be configured to selectively permit and/or restrict relative movement between the barrel 110 and the plunger 130. In some embodiments, the locking mechanism is an individual component that is separate from the barrel 110. In other embodiments, the locking mechanism is integrally formed with the barrel 110. In some embodiments, the locking mechanism comprises an elastomeric ring, which can be described as a locking ring. The locking ring can be an individual structure, or can comprise two or more subcomponents that may fit together to form a ring or like structure. The locking ring may have a variable radial thickness.

The locking mechanism may comprise a first interfering surface configured to engage the plunger 130, and a second surface configured to engage the barrel 110. In some embodiments, the first interfering surface is non-circular about the longitudinal axis of the syringe assembly 100, and the second surface is circular about the longitudinal axis of the syringe assembly 100. The first interfering surface may be, or may be disposed on, the inner surface of the locking mechanism, and the second surface may be, or may be disposed on, the outer surface of the locking member. Rotation of the plunger 130 may engage the locking mechanism to selectively create an interference fit between the locking mechanism and the plunger 130.

In some embodiments, the locking mechanism comprises a cam surface. As used herein, the term "cam surface" refers to a surface that is configured to transfer a rotational force into a linear force. For example, the cam surface may be a non-circular surface or a surface having non-uniform radius. The cam surface may be disposed on either a rotating member or the stationary member with which the rotating member interacts and/or engages. Thus, in some embodiments, the cam surface is disposed on the locking mechanism. For example, the cam surface may be disposed on an inner surface of a locking ring. In other embodiments, the cam surface is disposed on the plunger 130. For example, the plunger 130 may be elliptical in shape and the cam surface may be disposed on an exterior surface of the plunger 130.

Although not specifically depicted in FIG. 1, the barrel 110 may also comprise additional features or components that are commonly known in the art. For example, the barrel 110 may comprise indicia markings that may indicate specific volumes of fluid that may be drawn into or expelled from the barrel 110.

The plunger 130, or a portion thereof, is disposed within the barrel 110. The shape, size, and structure of the plunger 130 may vary as desired. In some embodiments, the plunger 130 comprises an elongate shaft 132 and one or more ribs 133. The ribs 133 may be configured to provide structure and support to the shaft 132, and may also engage with the locking mechanism.

The number of ribs 133 may vary as desired. For example, in some embodiments, the plunger 130 comprises as few as one rib 133. In other embodiments, the plunger 130 comprises two ribs 133. In other embodiments, the plunger 130 comprises three ribs 133. In yet other embodiments, the plunger 130 comprises four ribs 133. In still other embodiments, the plunger 130 comprises five or more ribs 133.

The ribs 133 may extend radially from the longitudinal axis $A_L$ of the shaft 132 and longitudinally along the length of the shaft 132. In some embodiments, the ribs 133 extend longitudinally along the entire length of the shaft 132. In other embodiments, the ribs 133 extend longitudinally along only a portion of the length of the shaft 132. The ribs 133 may also taper toward the proximal end 136 of the plunger 130 to facilitate use of the syringe assembly 100 by a practitioner. For example, the tapering of the ribs 133 may facilitate grasping the plunger 130.

The plunger 130 comprises a distal end 134 and a proximal end 136. In the illustrated embodiment, the distal end 134 is disposed within the barrel 110. The distal end 134 of the plunger 130 comprises a plunger head. In some embodiments, the plunger head is an individual component that is coupled to the distal end 134 of the plunger 130. In other embodiments, the plunger head is integral with the distal end 134 of the plunger 130. The plunger head may comprise a variety of elastomeric materials and may be configured to abut the inner surface of the barrel 110 and form a sealing engagement with the inner surface of the barrel 110. As can be appreciated, the plunger head is configured to be slideable within the barrel 110. In one embodiment, the plunger 130 is able to slide the length of the barrel 110 absent the engagement of a threaded member between the barrel 110 and the plunger 130.

As further shown in FIG. 1, the proximal end 136 of the plunger 130 may comprise a gripping member 137. The gripping member 137 facilitates use of the syringe assembly 100 by a practitioner. A variety of gripping members 137 may be used. In some embodiments, for example, the gripping member 137 comprises a circular disc or an elongated disc. In other embodiments, the gripping member 137 comprises a handle or like structures.

In some embodiments, the syringe assembly 100 is configured to be disposed in an unlocked configuration. In the unlocked configuration, the plunger 130 is moveable within the barrel 110 by a practitioner. For example, the plunger 130 is moveable along the longitudinal axis $A_L$ of the syringe assembly 100, without restriction. The plunger 130 may thus be described as being longitudinally moveable, or longitudinally displaceable, within the barrel 110.

The syringe assembly 100 is also configured to be disposed in a locked configuration. When in the locked configuration, longitudinal movement of the plunger 130 is restricted or substantially restricted. Transition between the unlocked configuration and the locked configuration may occur in various ways. In some embodiments, for example, transitioning the syringe assembly 100 from an unlocked configuration to a locked configuration, and vice versa, comprises rotating the plunger 130 about the longitudinal axis $A_L$. The plunger 130 may thus be described as being axially rotatable, or configured to rotate axially, within the barrel 110. In some embodiments, axial rotation of the plunger 130 results in engaging the locking mechanism. When engaged, the locking mechanism restricts or substantially restricts longitudinal movement of the plunger 130 within the barrel 110.

The syringe assembly 100 may further comprise a tactile indicator that is encountered when transitioning from the unlocked configuration to the locked configuration or vice versa. The tactile indicator may signal to the practitioner that the syringe assembly has transitioned to the locked configuration or the unlocked configuration. For example, a practitioner can rotate the plunger from the locked configuration to the unlocked configuration and vice versa, and feel the tactile indicator during the transition. The practitioner may thereafter refrain from additional axial rotation of the plunger 130.

FIG. 2 is another perspective view of the syringe assembly 100 of FIG. 1. As shown in FIG. 2, the syringe assembly 100 comprises a barrel 110, a plunger 130, and a locking mechanism 150. The locking mechanism 150 is shown disposed within a seating region 119 that is located near the proximal end 116 of the barrel 110. The plunger 130 is shown disposed such that it is engaged with and extends through the locking mechanism 150 and into the barrel 110.

FIG. 3 is a side view of the syringe assembly 100 of FIG. 1. As shown in FIG. 3, the syringe assembly 100 comprises a barrel 110, a plunger 130, and a locking mechanism. The distal end 134 of the plunger 130 is shown disposed within the barrel 110. The distal end 134 of the plunger 130 is further shown comprising a plunger head 131. As previously discussed, the plunger head 131 may provide a fluid sealing engagement with the inner surface of the barrel 110.

FIGS. 4-5 are end views of the syringe assembly 100 of FIG. 1. FIG. 4 shows the opening 115, the fitting 113, and the seating region 119 of the syringe assembly 100. FIG. 4 also shows a gripping member 117 extending outwardly from the barrel 110. FIG. 5 shows a gripping member 117 of the barrel and a gripping member 137 of the plunger.

FIG. 6 is a cross-sectional side view of the syringe assembly 100 of FIG. 1. More specifically, FIG. 6 is a cross-sectional view taken along view line 6-6 of FIG. 4. As shown in FIG. 6, the syringe assembly 100 comprises a barrel 110, a plunger 130, and a locking mechanism 150. The locking mechanism 150 is disposed between the barrel 110 and the plunger 130. As further shown in FIG. 6, the locking mechanism 150 may be constrained to the seating region 119 such that it does not extend beyond the seating region 119.

A portion of the plunger 130 is disposed within the barrel 110. The distal end 134 of the plunger 130 comprises a plunger head 131. The plunger head 131 is shown abutting the inner surface 120 of the barrel 110. Thus the plunger 130 is configured to sealingly engage the inner surface 120 of the barrel 110.

FIGS. 7-8 are exploded perspective views of the syringe assembly 100 of FIG. 1. As shown in FIGS. 7-8, the syringe assembly 100 comprises a barrel 110, a plunger 130, and a locking mechanism 150. FIGS. 7-8 further depict the plunger head 131, which is coupled to the plunger 130.

As shown in FIG. 8, the seating region 119 may be configured to retain the locking mechanism 150. For example, the inner surface 125 of the seating region 119 may comprise one or more protrusions 122 that extend inwardly. The protrusions 122 are configured to restrict axial rotation of the locking mechanism 150 when it is disposed within the seating region 119. The barrel 110 and/or seating region 119 may further comprise one or more retaining ridges 124. The retaining ridges 124 extend inwardly from a proximal edge 121 of the opening of the barrel 110 and are configured to restrict longitudinal movement of the locking mechanism 150. For example, the retaining ridges 124 keep the locking mechanism 150 from coming out or falling out of the barrel 110, especially when a practitioner retracts the plunger 130.

As shown in FIGS. 7-8, the locking mechanism 150 may be a substantially cylindrical-shaped ring and is thus described as a locking ring. The locking mechanism 150 may comprise a lumen extending therethrough to receive the plunger 130. In some embodiments, the locking mechanism 150 comprises an elastomeric material. The locking mechanism 150 also comprises an outer surface 152 and an inner surface 154. The inner surface 154 may comprise one or more protrusions 156 that extend inwardly from the inner surface 154 and are configured to abut the ribs 133 on the plunger 130. The outer surface 152 may comprise one or more slots 153. When disposed within the barrel 110, the slots 153 may be aligned with and configured to engage with one or more protrusions 122 disposed on an inner surface 120 of the barrel 110. Thus the protrusions 122 and the slots 153 are configured to retain the locking mechanism 150 in substantially a fixed position within the barrel 110.

FIGS. 9-10 are cross-sectional views of the syringe assembly 100, also taken along view lines 6-6, depicting illustrative longitudinal movement of the plunger 130 within the barrel 110. In FIG. 9, the plunger 130 is longitudinally disposed within the barrel 110 at an inward, i.e., distal position. In FIG. 10, the plunger 130 is longitudinally disposed within the barrel 110 at an intermediate position. As can be appreciated, when the syringe assembly 100 is in an unlocked configuration, a practitioner may grasp the gripping member 137 of the plunger 130 and withdraw the plunger 130 outwardly, for example from the inward longitudinal position of FIG. 9 to the intermediate longitudinal position of FIG. 10. As the plunger 130 is withdrawn, a negative gauge pressure or vacuum is established within the barrel 110. This negative gauge pressure biases the plunger 130 toward returning to a more longitudinally inward position. To facilitate maintaining the negative gauge pressure within the barrel 110, the practitioner may axially rotate the plunger 130, thereby transitioning the syringe assembly 100 from an unlocked configuration to a locked configuration. In the locked configuration, longitudinal movement of the plunger 130 is restricted or substantially restricted.

The syringe assembly 100 is configured to transition from the unlocked configuration to the locked configuration at any position along a continuous portion of the length of the barrel 110. The plunger 130 is thus configured to be lockable within the barrel 110 at any desired longitudinal position along the portion of the length of the barrel 110 within which the plunger 130 is longitudinally displaceable.

FIGS. 11A-11C are cross-sectional views of a syringe assembly 100, taken along the view line 11-11, in an unlocked configuration (FIG. 11A), in a locked configuration (FIG. 11B), and at an intermediate position at a transition between the unlocked configuration and the locked configuration (FIG. 11C). As shown in FIGS. 11A-11C, the plunger and the locking mechanism 150 engage during the transition between the unlocked configuration (FIG. 11A) and the locked configuration (FIG. 11B). For example, the locking mechanism 150 may comprise one or more locking surfaces 160, each of which may be configured to engage with a rib 133 of the plunger. In some embodiments, the locking surfaces 160 are disposed on the inner surface 154 of the locking mechanism 150 between two adjacent protrusions 156 that are also disposed on the inner surface 154 of the locking mechanism 150.

The number of locking surfaces 160 disposed on the locking mechanism 150 may vary. In some embodiments, the number of locking surfaces 160 may be dependent upon the number of ribs 133 on the associated plunger. For example, as shown in FIGS. 11A-11C, a locking mechanism 150 comprising four locking surfaces 160 and may be configured for use with a plunger comprising four ribs 133. Each rib 133 may be configured to engage with its own, corresponding locking surface 160.

The locking mechanism 150 may comprise one or more radially expanding components. For example, as shown in FIGS. 11A-11C, in some embodiments, the distance (e.g., $D_1$, $D_2$, $D_3$) between the locking surface 160 and the center axis of the locking mechanism 150 varies along the length of the locking surface 160. This distance (e.g., $D_1$, $D_2$, $D_3$) may be described as the inner radius of the locking mechanism 150. As shown in FIGS. 11A-11C, the variation in the distance (e.g., $D_1$, $D_2$, $D_3$) is the direct result of varying the thickness, or radial thickness, of the locking mechanism 150 between protrusions 156.

In some embodiments, the distance $D_1$ or inner radius at a first region 161 of the locking surface 160 is greater than the distance $D_2$ or inner radius at an intermediate region 162 of the locking surface 160, which is greater than the distance $D_3$ or inner radius at a second region 163 of the locking surface 160. Thus, in some embodiments, $D_1>D_2>D_3$. In other embodiments, the distance $D_1$ or inner radius at the first region 161 of the locking surface 160 is greater than the distance $D_2$ or inner radius at the intermediate region 162 of the locking surface 160, which is equal to the distance $D_3$ or inner radius at the second region 163 of the locking surface 160. Thus, in some embodiments, $D_1>D_2=D_3$. Accordingly as shown in FIGS. 11A-11C, the distance or inner radius of the locking surface 160 gradually decreases from the first region 161 to the intermediate region 162. Thereafter, in some embodiments, the distance or inner radius of the locking surface 160 remains constant from the intermediate region 162 to the second region 163. This change in radius between $D_1$ and $D_2$ along the locking surface 160 is one example of the locking surface 160 being a cam surface.

In some embodiments, the length of the ribs 133 is equal to or less than the length of the distance $D_1$ or inner radius at the first region 161. Thus the engagement of the ribs 133 and the locking surface 160 at the first region 161 may be minimal. The length of the ribs 133 may, however, be greater than the distance $D_2$ or inner radius at the intermediate region 162 and the distance $D_3$ or inner radius at the second region 163. Thus the engagement of the ribs 133 with the locking surface 160 at the intermediate region 162 and/or the second region 163 applies a greater compression force against the locking surface 160, resulting in an interference fit. In some embodiments, the compression force, or interference fit, between the ribs 133 and the locking surface 160 at the intermediate region 162 and/or second region 163 restricts longitudinal movement of the plunger.

As can be appreciated, axial rotation of the plunger from a position wherein a rib 133 abuts the locking surface 160 at the first region 161 to a position wherein the rib 133 abuts the locking surface 160 at the intermediate region 162 requires force. Further, the force required gradually increases as the distance from the center axis of the locking mechanism 150 (or the inner radius) decreases along the locking surface 160 from the first region 161 to the intermediate region 162. In contrast, in some embodiments, the force required to rotate the plunger from the intermediate region 162 to the second region 163 remains constant. Rotating the plunger from the intermediate position (FIG. 11C) to the locked configuration (FIG. 11B) may thus feel different to the practitioner as compared to the initial rotation of the plunger from the unlocked configuration (FIG. 11A) to the intermediate position (FIG. 11C). This difference signals that the syringe assembly has nearly, or completely, transitioned from an unlocked configuration (FIG. 11A) to a locked configuration (FIG. 11B). This transition through the intermediate position may thus be described as functioning as a tactile indicator. The tactile indicator may also be felt by the practitioner during a transition from the locked configuration (FIG. 11C) to the unlocked configuration (FIG. 11A).

With reference to FIG. 11A, the syringe assembly 100 is shown in an unlocked configuration. The ribs 133 are aligned and positioned to abut a first region 161 of the locking surface 160. At the first region 161, the distance $D_1$ or inner radius is at a maximum. As further shown in FIG. 11A, the thickness of the locking mechanism 150 may be at a minimum in the first region 161. Because the distance $D_1$ or inner radius at the first region 161 may be substantially the same length, or less than a radial length of the ribs 133, engagement between the ribs 133 and the locking mechanism 150 is at a minimum (or not engaged at all), and the plunger is longitudinally moveable within the barrel.

With reference to FIG. 11B, the syringe assembly 100 is shown in a locked configuration, wherein the plunger has been axially rotated between about 80° and about 90° from the unlocked configuration of FIG. 11A. The term "about" refers to a range of ±10°. As shown in FIG. 11B, in the locked configuration, the ribs 133 are aligned and positioned to abut the second region 163 of the locking surface 160. At the second region 163, the distance $D_3$ or inner radius is at a minimum, or alternatively less than distance $D_1$. As further shown in FIG. 11B, the thickness of the locking mechanism 160 may be at a maximum near the second region 163.

As previously discussed, the distance $D_3$ or inner radius is less than the radial length of the ribs 133. The practitioner may thus exert force when axially rotating the plunger towards the locked configuration of FIG. 11B. Because the radial length of the ribs 133 is greater than $D_3$, the ribs 133 exert a radially outward force upon the locking mechanism 150 which compresses the locking mechanism 150. The locking mechanism 150 is then biased toward an uncompressed state and may thus exert a reactionary force upon the ribs 133. This engagement between the locking mechanism 150 and the ribs 133 can create an interference fit and restrict or substantially restrict longitudinal movement of the plunger within the barrel.

With reference to FIG. 11C, the syringe assembly 100 is shown in an intermediate position, wherein the plunger has been axially rotated about 45°. In other embodiments, the intermediate position is a position wherein the plunger is axially rotated between about 30° and about 75°. As shown in FIG. 11C, in the intermediate position, the ribs 133 are aligned and positioned to abut an intermediate region 162 of the locking surface 160. In some embodiments, the distance $D_2$ or inner radius is between the distances $D_1$ and $D_3$ depicted above in FIGS. 11A-11B. In other embodiments, the distance $D_2$ or inner radius is equal to the distance $D_3$ or inner radius depicted in FIG. 11B.

Similar to the locked configuration, in the intermediate position, the distance $D_2$ or inner radius is less than the radial length of the ribs 133. The practitioner may thus exert force when axially rotating the plunger toward the intermediate position of FIG. 11C. Because the length of the ribs 133 is greater than $D_2$, the ribs 133 exert an outward force upon the locking mechanism 150 which compresses the locking mechanism 150. The locking mechanism 150 is then biased toward an uncompressed state and thus exerts a reactionary force upon the ribs 133. This engagement or interference fit between the locking mechanism 150 and the ribs 133 restricts or substantially restricts longitudinal movement of the plunger within the barrel.

Figure 14:
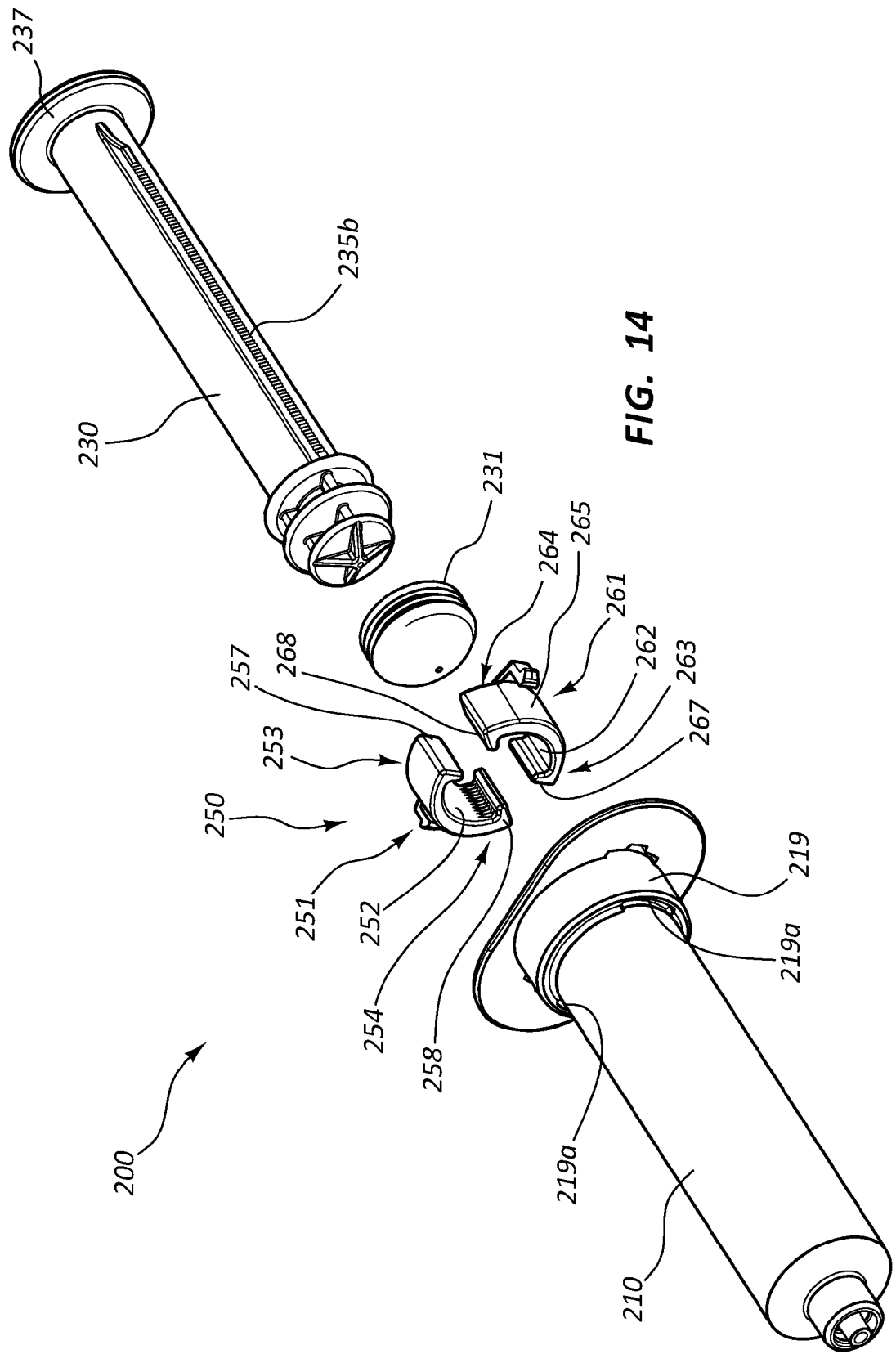
FIG. 14 is an exploded view of the syringe assembly of FIG. 12.
Figure 15:
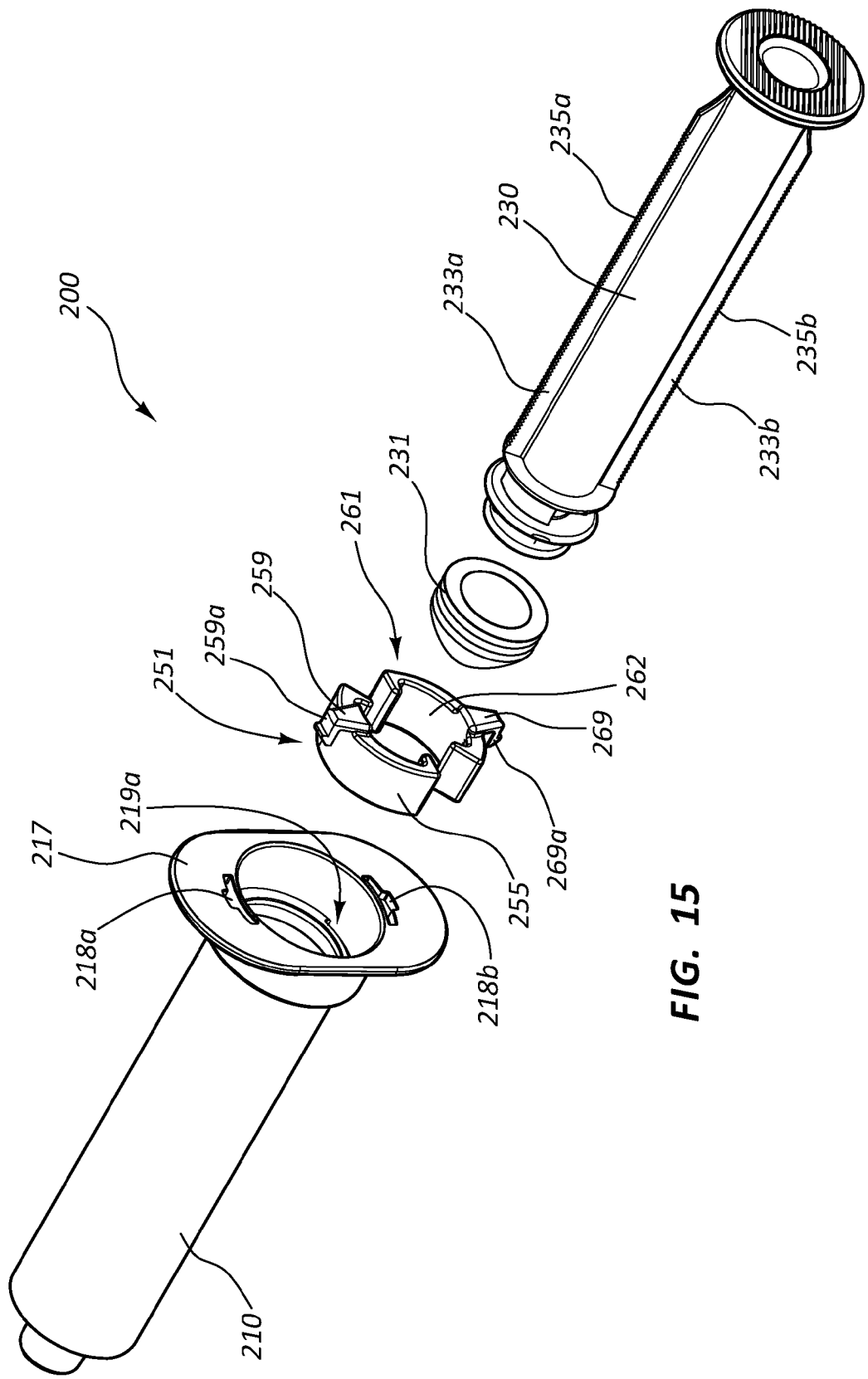
FIG. 15 is another exploded view of the syringe assembly of FIG. 12.

FIGS. 12-16C illustrate another embodiment of a syringe assembly, a syringe assembly 200. FIGS. 12 and 13 are perspective views of a syringe assembly 200. FIGS. 14 and 15 illustrate exploded views of the syringe assembly 200. The syringe assembly 200 is similar to the syringe assembly 100; however, the locking mechanism is different. It should be understood that the disclosure above regarding components of the syringe assembly 100 also applies to like components of the syringe assembly 200. Likewise, disclosure regarding components of the syringe assembly 200 applies to like components of the syringe assembly 100.

As shown in FIGS. 12 and 13, the syringe assembly 200 may comprise a barrel 210, a plunger 230, and a locking mechanism 250. Similar as with the locking mechanism 150, when engaged, the locking mechanism 250 is configured to restrict longitudinal movement of the plunger 230 within the barrel 210. The locking mechanism 250 may be configured to restrict or allow longitudinal movement of the plunger 230 based on the rotational position of the plunger 230.

In the illustrated embodiment, the locking mechanism 250 comprises a first partial ring 251 and a second partial ring 261. In other embodiments, only the first partial ring 251 may be present or more than two partial rings may be present. In some embodiments, the locking mechanism 250 comprises the first partial ring 251, wherein it has a variable radial thickness.

In the illustrated embodiment, the plunger 230 applies a radial force to the first and second partial rings 251, 261 when in a locked configuration. The plunger 230 may comprise a raised surface 235a that applies the radial force to the first partial ring 251. Likewise, the plunger 230 may comprise a raised surface 235b that applies the radial force to the second partial ring 261. The raised surfaces 235a, 235b may apply a minimal radial force to the first and second partial rings 251, 261 when in an unlocked configuration. In the illustrated embodiment, the outer surface of the rib 233a comprises the raised surfaces 235a and the outer surface of the rib 233b comprises the raised surfaces 235b. The number of ribs 233 on the plunger 230 may equal the number of partial rings.

The plunger 230 may comprise a plunger head 231. The proximal end of the plunger 230 may comprise a gripping member 237. A variety of gripping members 237 may be used. In some embodiments, for example, the gripping member 237 comprises a circular disc or an elongated disc. In other embodiments, the gripping member 237 comprises a handle or like structures.

In the illustrated embodiment, the first and second partial rings 251, 261 each comprise a rigid material. In other embodiments, the first and second partial rings 251, 261 may comprise an elastomeric material.

In the illustrated embodiment, the first partial ring 251 comprises a first cam surface 252. The first cam surface 252 may comprise a non-uniform surface disposed on an inner surface of the first partial ring 251, such as in the illustrated embodiment. For example, in the illustrated embodiment, the non-uniform surface comprises a non-circular arcuate surface extending from about a narrow end 253 of the first partial ring 251 to about a thick end 254 of the first partial ring 251.

Likewise, the second partial ring 261 may comprise a second cam surface 262, such as in the illustrated embodiment. The second cam surface 262 may comprise a non-uniform surface disposed on an inner surface of the second partial ring 261. The non-uniform surface of the second cam surface 262 may comprise a non-circular arcuate surface extending from about a narrow end 263 of the second partial ring 261 to about a thick end 264 of the second partial ring 261.

In the illustrated embodiment, an outer surface 255 of the first partial ring 251 comprises a circular arcuate surface. Likewise, an outer surface 265 of the second partial ring 261 comprises a circular arcuate surface. The outer surfaces 255, 265 may be configured to mate with an inner surface of the barrel 210. In other embodiments, the outer surfaces 255, 265 may comprise cam surfaces.

In the illustrated embodiment, the first partial ring 251 comprises a first end stop 257. The first end stop 257 may comprise a protrusion extending radially inward from the narrow end 253 of the first partial ring 251. The first end stop 257 may be sized and located to prevent rotation of the rib 233a of the plunger 230 beyond the narrow end 253.

In the illustrated embodiment, the first partial ring 251 further comprises a second end stop 258. The second end stop 258 may comprise a protrusion extending radially inward from the thick end 254 of the first partial ring 251. The second end stop 258 may be sized and located to prevent rotation of the rib 233a beyond the thick end 254. Ridges 252a may be formed on the inner surface (first cam surface 252) at the thick end 254 near or adjacent the second end stop 258. The ridges 252a may be oriented and sized so as to resist longitudinal movement of the plunger 230 when the rib 233a is engaged with the ridges 252a. The ridges 252a may also be sized and orientated so as to engage with teeth formed on the raised surface 235a of the rib 233a. Likewise, in the illustrated embodiment, the second partial ring 261 comprises a first end stop 267. The first end stop 267 may comprise a protrusion extending radially inward from the narrow end 263 of the second partial ring 261. The first end stop 267 may be sized and located to prevent rotation of the rib 233b of the plunger 230 beyond the narrow end 263.

In the illustrated embodiment, the second partial ring 261 further comprises a second end stop 268. The second end stop 268 may comprise a protrusion extending radially inward from the thick end 264 of the second partial ring 261. The second end stop 268 may be sized and located to prevent rotation of the rib 233b beyond the thick end 264. Ridges 262a may be formed on the inner surface (second cam surface 262) at the thick end 264 near or adjacent the second end stop 268. The ridges 262a may be oriented and sized so as to resist longitudinal movement of the plunger 230 when the rib 233b is engaged with the ridges 262a. The ridges 262a may also be sized and orientated so as to engage with teeth formed on the raised surface 235b of the rib 233b.

In other embodiments, the ridges 252a, 262a may or may not be present, but the raised surfaces 235a, 235b are smooth. In still other embodiments, the ridges 252a, 262a are not present, but the raised surfaces 235a, 235b may or may not comprise teeth.

In some embodiments, all or a portion of the first and second cam surfaces 252, 262 may be configured to function as a cam. For example, in the illustrated embodiment, the portion of the first cam surface 252 between the first end stop 257 and the ridges 252a may be configured to function as a cam as the first partial ring 251 increases in thickness. The portion of the first cam surface 252 at or near where the ridges 252a are formed may not be configured to function as a cam, or stated another way, the thickness of the first partial ring 251 at or near the ridges 252a may stay the same or may decrease relative to the thickness of the first partial ring 251 adjacent the ridges 252a. The second cam surface 262 may be similarly configured.

In the illustrated embodiment, the first and second partial rings 251, 261 are located inside the proximal end of the barrel 210. In the illustrated embodiment, the first and second partial rings 251, 261 are configured to engage with the barrel 210 to retain the first and second partial rings 251, 261 within the barrel 210. For example, in the illustrated embodiment, the first partial ring 251 comprises a first retaining arm 259 configured to engage with the barrel 210 to retain the first partial ring 251 within the barrel 210. Likewise, the second partial ring 261 may comprise a second retaining arm 269 configured to engage with the barrel 210 to retain the second partial ring 261 within the barrel 210. For example, the first retaining arm 259 may comprise a first latch 259a configured to engage with a first receptacle 218a in the barrel 210 and the second retaining arm 269 may comprise a second latch 269a configured to engage with a second receptacle 218b in the barrel 210. The first and second receptacles 218a, 218b may be located in a gripping member 217. The first and second receptacles 218a, 218b and the first and second retaining arms 259, 269 may engage in a snap-fit type configuration with mating detents, ridges, latches, or other components. One of skill in the art, with the aid of the present disclosure, would understand that other structures may be used to retain the first and second partial rings 251, 261 within the barrel 210.

In the illustrated embodiment, the barrel 210 further comprises a seating region 219 at the proximal end, and wherein the first and second partial rings 251, 261 are disposed within the seating region 219. The seating region 219 may be configured to retain the first and second partial rings 251, 261 in the barrel 210. The seating region 219 may comprise a greater inner diameter than the inner diameter of a remainder of the barrel 210. The seating region 219 may comprise one or more apertures 219a located and configured to allow the inner diameter of the seating region 219 to deform outward as the plunger 230 applies a radial force to the first and second partial rings 251, 261. This outward deformation may add compliance to the locking mechanism, facilitating rotational displacement of the plunger during locking or unlocking, while still providing radial constrain such that the plunger frictionally engages the first and second partial rings 251, 261 when the assembly is in a locked position. In other embodiments, the seating region 219 may not be present or may be adapted to engage with particular embodiments of the locking mechanism 250.

FIGS. 16A-16C illustrate operation of the locking mechanism 250. FIG. 16A illustrates a cross-sectional view of the proximal end of the syringe assembly 200 in the locked configuration, taken along the view line 16-16. Rib 233a has been rotated clockwise against the second end stop 258. Likewise, rib 233b has been rotated clockwise against the second end stop 268. The raised surface 235a (outer surface of the rib 233a) is engaged with the ridges formed on the inner surface (first cam surface 252) of the first partial ring 251. Likewise, the raised surface 235b (outer surface of the rib 233b) is engaged with the ridges formed on the inner surface (second cam surface 262) of the second partial ring 261. In the illustrated embodiment, the ridges and the corresponding second end stops 258, 268 serve as a tactile indicator that the plunger 230 has been rotated to the locked configuration. In other embodiments, other mechanisms for providing a tactile indicator may be used. For example, and as further detailed below, the first and second cam surfaces 252, 262 may be shaped or designed to provide a tactile and/or audible indication the assembly has been disposed in the locked configuration.

FIG. 16B illustrates a cross-sectional view of the proximal end of the syringe assembly 200 in the unlocked configuration, taken along the view line 16-16. Rib 233a has been rotated counter-clockwise against the first end stop 257. Likewise, rib 233b has been rotated counter-clockwise against the first end stop 267. In the illustrated embodiment, the raised surfaces 235a, 235b are shown as remaining in contact with the corresponding first and second cam surfaces 252, 262. In some embodiments, when in the unlocked configuration, the raised surfaces 235a, 235b may not be in contact with the corresponding first and second cam surfaces 252, 262. For example, when in the unlocked configuration, one or both of the raised surfaces 235a, 235b may lightly contact the corresponding first and second cam surfaces 252, 262 (i.e., apply a minimal radial force), such that the plunger 230 loosely fits together with the first and second partial rings 251, 262. In another example, when in the unlocked configuration, one or both of the raised surfaces 235a, 235b may lightly contact (i.e., apply a minimal radial force) the corresponding first and second cam surfaces 252, 262, such that interaction between the surfaces can be heard and/or felt by a practitioner as the plunger 230 is moved longitudinally within the barrel 210.

FIG. 16C illustrates a cross-sectional view of the proximal end of the syringe assembly 200 with the plunger 230 in a partially locked position, taken along the view line 16-16. Ribs 233a, 233b have been rotated about 45 degrees away from the first end stops, 257, 267, respectively. At about this rotational point the raised surfaces 235a, 235b may begin to frictionally engage with the first and second cam surfaces 252, 262 sufficient to restrict or partially restrict longitudinal movement of the plunger 230. As the plunger 230 is further rotated clockwise, the frictional engagement will increase, further restricting longitudinal movement of the plunger 230. In some embodiments, the plunger 230 is axially rotated between about 80 degrees and about 130 degrees to transition from the unlocked configuration to the locked configuration.

In the illustrated embodiment, the seating region 219 comprises two apertures 219a. As discussed previously, the apertures 219*a* may be located and configured to allow the inner diameter of the seating region 219 to deform outward as the plunger 230 applies a radial force to the first and second partial rings 251, 261. In the illustrated embodiment, the apertures 219*a* are located about 90 degrees from the first end stops 257, 267, respectively, and do not overlap with the second end stops 258, 268, respectively. This provides the benefit that as radial force is applied to the first and second partial rings 251, 261 at the location of the apertures 219*a*, that the seating region 219 may deform, potentially imperceptibly to a practitioner, outwardly at that location.

In the illustrated embodiment, the thickness of the first partial ring 251 at or near the ridges 252*a* stays the same or decreases relative to the thickness of the first partial ring 251 adjacent the ridges 252*a* and likewise for the second partial ring 252. As a result, a practitioner experiences increased resistance as the plunger 230 is rotated clockwise beyond the position illustrated in FIG. 16C and while the ribs 233*a*, 233*b* are near the apertures 219*a*. Then, as the ribs 233*a*, 233*b* approach the ridges 252*a*, 262*a*, there is a noticeable decrease in resistance to rotation. Next, there is a marked increase in resistance as the ribs 233*a*, 233*b* contact the second end stops 258, 268. One benefit of the temporary decrease in resistance during rotation of the plunger 230 to the locked configuration is that it provides a tactile indication to the practitioner that the plunger 230 has been rotated to the locked configuration.

Figure 17B:
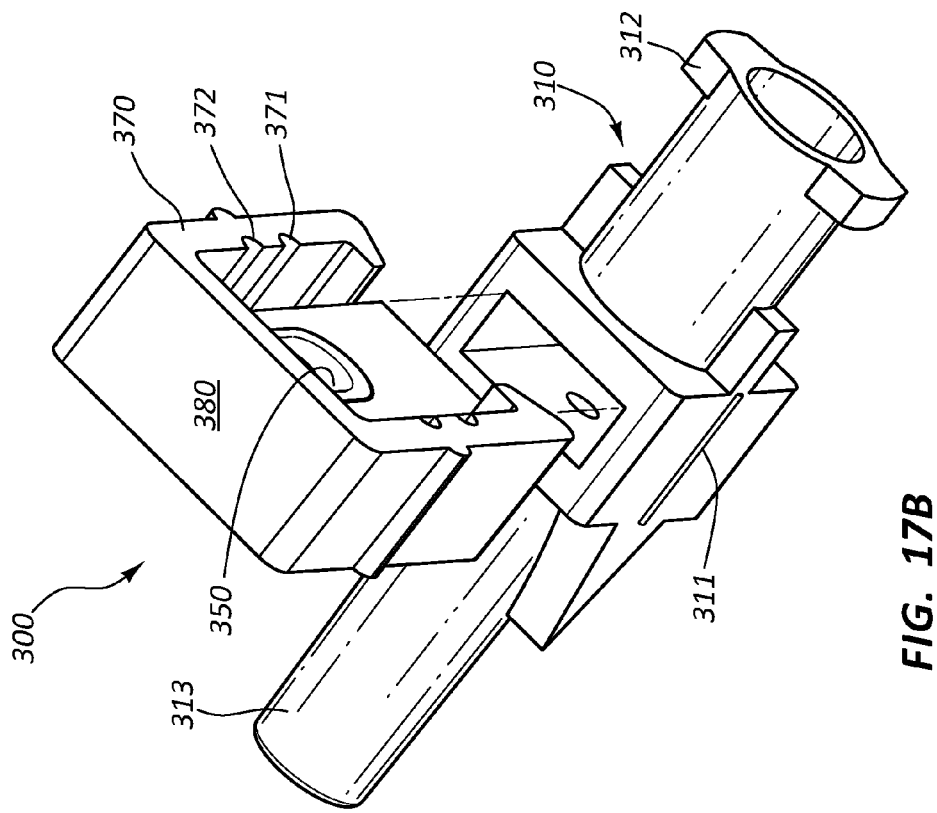
FIG. 17B is a partially exploded view of the valve of FIG. 17A.
Figure 17A:
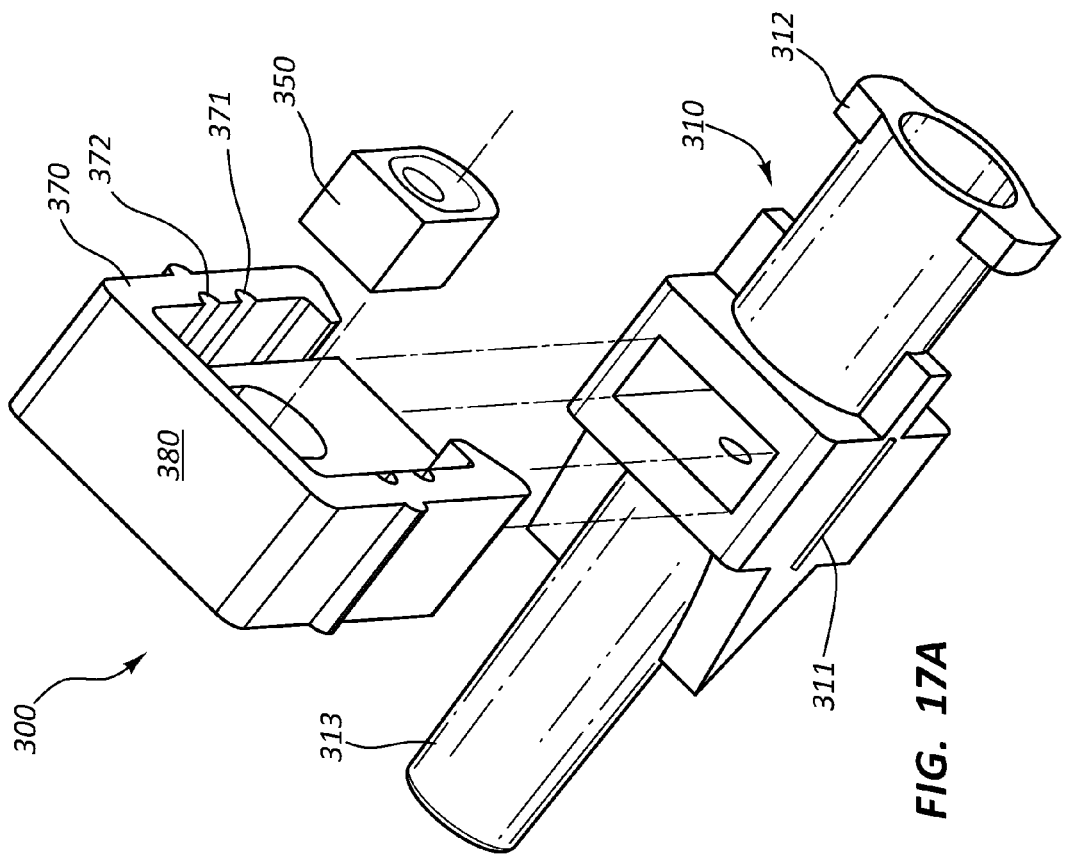
FIG. 17A is an exploded view of one embodiment of a valve.

The present disclosure also includes valves for maintaining a vacuum in a syringe. FIGS. 17A-18B illustrate one embodiment of a valve, a valve 300. FIG. 17A is an exploded view of the valve 300 and FIG. 17B is a partially assembled view of the valve of FIG. 17A. The valve 300 comprises a body portion 310 comprising a fluid channel 320 configured to fluidically couple a syringe, such as the syringe assembly 100 or the syringe assembly 200, and a body insertion device, such as a needle or a catheter. For example, the proximal end 312 may be configured to mate with the tip of a syringe and the distal end 313 may be configured to mate with a body insertion device. The valve 300 further comprises a valve member 350 configured to fluidically seal the fluid channel 320 sufficient to maintain a vacuum in the syringe and operably connected to the body portion 310 so as to block the fluid channel 320 unless actuated. The valve 300 further comprises an actuator 370 operably connected to the valve member 350 and configured to move the valve member 350 sufficient to unblock the fluid channel 310. The actuator 370 may be configured to be actuated with one hand.

In the illustrated embodiment, the actuator 370 is configured to linearly actuate the valve member 350. In other embodiments, the actuator may be configured to rotationally actuate the valve member.

The actuator 370 may have a first position and a second position. In such embodiments, such as the illustrated embodiment, the actuator 370 is in the first position when the valve member 350 is positioned so as to block the fluid channel 320. Likewise, in such embodiments, the actuator 370 is in the second position when the valve member 350 is positioned so as to at least partially unblock the fluid channel 320.

In the illustrated embodiment, the valve body 310 comprises a shoulder 311 on either side of the valve body 310. The actuator 370 comprises clip arms configured to grip the sides of the valve body 310. The clip arms includes first grooves 371 and second grooves 372. The first grooves 371 are lower on the clip arms than the second grooves 372. The first grooves 371 and the second grooves 372 are both configured to mate with the shoulders 311, although not at the same time.

Figure 18A:
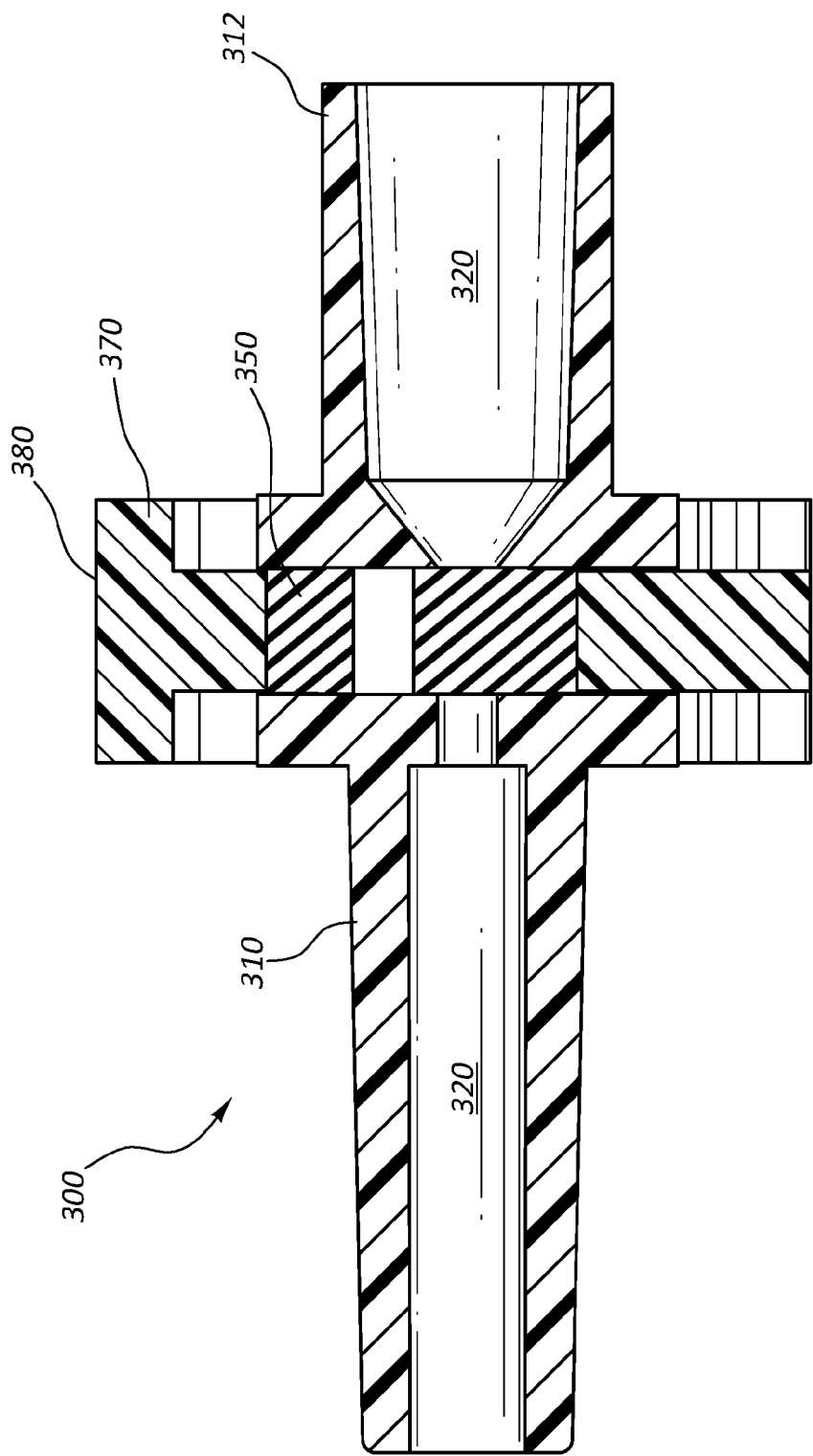
FIG. 18A is a cross-sectional view of the valve illustrated in FIG. 17C, taken along the view line 18A-18A.

When the actuator 370, with the seal member 350 in place, is engaged with the body portion 310, such as illustrated in FIG. 17C, then the shoulders 311 are mated with the first grooves 371 and the valve 300 is in the first position. FIG. 18A is a cross-sectional view of the valve 300 in the first position, taken along the view line 18A-18A. In the first position the fluid channel 320 is blocked. All or a portion of the seal member 350 may comprise elastomeric materials to facilitate maintaining a vacuum in the proximal end of the fluid channel 320 (corresponding to the proximal end 312 of the valve body 310).

Figure 18B:
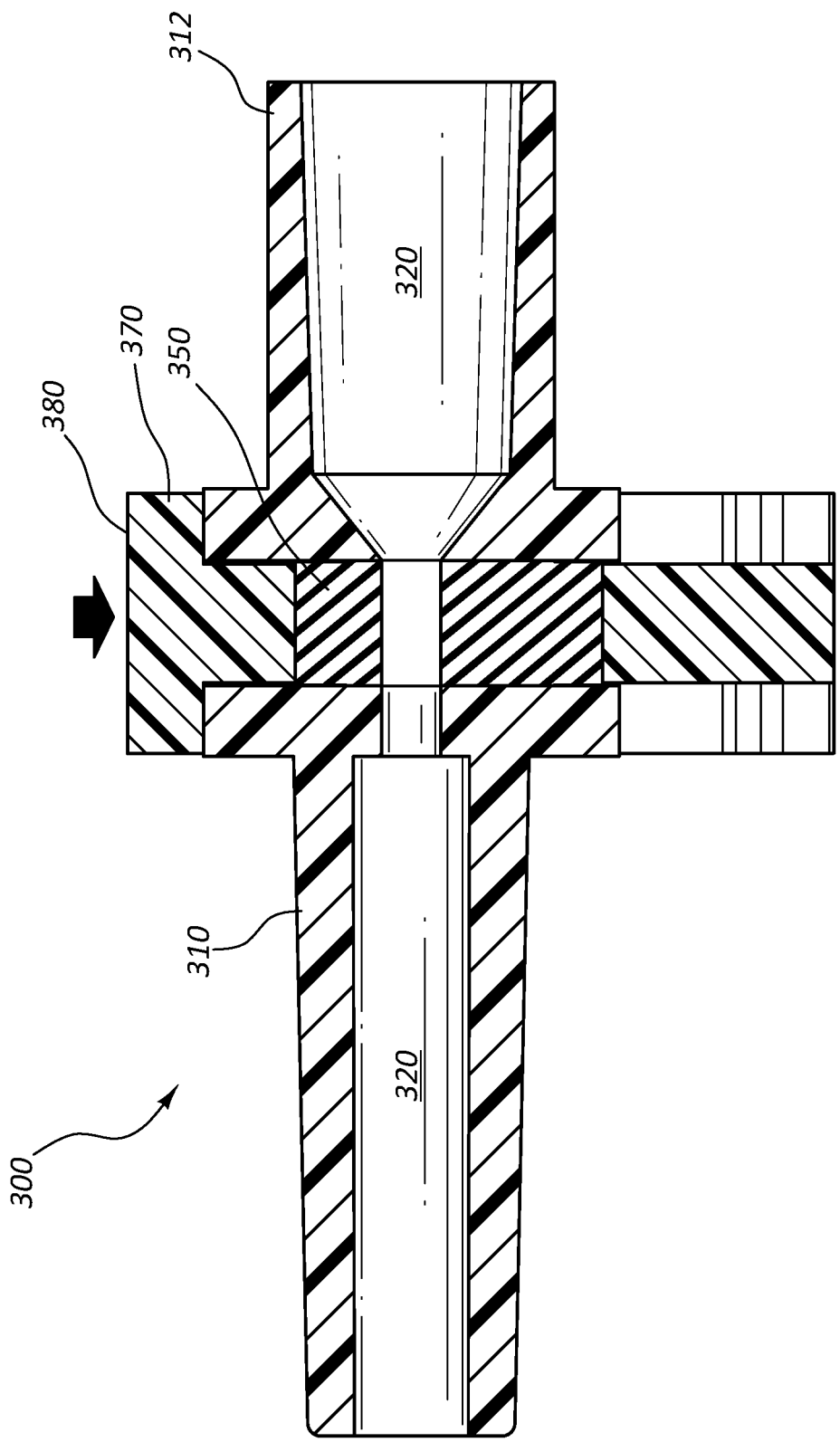
FIG. 18B is a cross-sectional view of the valve illustrated in FIG. 17D, taken along the view line 18B-18B.

When the actuator 370, with the seal member 350 in place, is engaged with the body portion 310, such as illustrated in FIG. 17D, then the shoulders 311 are mated with the second grooves 372 and the valve 300 is in the second position. FIG. 18B is a cross-sectional view of the valve 300 in the second position, taken along the view line 18B-18B. In the second position the fluid channel 320 is fully unblocked.

In some embodiments, such as the illustrated embodiment, the actuator 370 comprises a depressible surface 380 configured to move the actuator 370 from the first position to the second position. The actuator 370 may be configured to stay in the second position after pressure is released from the depressible surface 380, such as in the illustrated embodiment. Alternatively, the actuator 370 may be configured to return to the first position after pressure is released from the depressible surface 380. For example, the actuator 370 may comprises a spring member configured to return the valve member 350 to a blocking position after pressure is released from the depressible surface 380.

The embodiments of valves disclosed herein may be used with any of the embodiments of the syringe assemblies disclosed herein, such as the syringe assemblies 100 and 200. Additionally, the syringe assemblies 100 and 200 may comprise a valve configured to maintain a vacuum in the barrel 110, 210 between the plunger 130, 230 and the valve. In some embodiments, the valve may be integrated into barrel 110, 210, such as into the distal end thereof.

In some embodiments, the valve may be disposed in a closed configuration as a practitioner draws the plunger in a proximal direction. Proximal displacement of the plunger may result in negative gauge pressure, or a partial vacuum, within the barrel. The practitioner may then lock the plunger in a proximal position. The valve, in the closed position, and the locked plunger, may then maintain the partial vacuum within the barrel without input from the practitioner. In some instances, the valve may be actuated with the same hand a practitioner is using to grip the assembly. In other words, in some embodiments the components are disposed such that a practitioner may hold the syringe, and actuate the valve, with one hand. For example, with the plunger locked, the valve closed, and negative gauge pressure within the barrel, the practitioner may dispose the assembly such that the fluidic channel of the valve is adjacent an item to be captured, such as a thrombus within a patient's body. The practitioner may then open the valve and the thrombus may be drawn through the valve into the barrel as the partial vacuum within the barrel draws material through the valve. The barrel and valve may then be used as a storage or transportation device for the captured sample.

Methods of using the lockable syringe assembly are also disclosed herein. For example, the lockable syringe assembly may be used in methods of applying a negative gauge pressure to a patient. The methods may also be used in withdrawing fluid from a patient. The methods may comprise a step of obtaining a lockable syringe assembly as described herein. For example, the syringe assembly can comprise a barrel, a plunger, and a locking mechanism comprising a cam surface. The methods may further comprise a step of withdrawing the plunger within the barrel to establish a negative gauge pressure within the barrel. The methods may further comprise a step of axially rotating the plunger with respect to the barrel such that the cam surface transitions from an unlocked configuration to a locked configuration to maintain negative gauge pressure within the barrel. In some embodiments, the step of axially rotating the plunger may comprise applying a radial force against the cam surface. In some embodiments, the step of applying a radial force may comprise applying a radial force to an elastomeric ring. In some embodiments, the step of applying a radial force may comprise applying a radial force to a rigid partial ring.

In some embodiments, the methods may further comprise depressing a valve actuator to fluidically couple the syringe assembly to a body insertion device, such as a needle or catheter, and release the negative gauge pressure in the barrel. Additionally, in some embodiments, depressing the valve actuator comprises depressing a valve actuator integrated with the barrel. Alternatively, in other embodiments, depressing the valve actuator comprises depressing a valve actuator external to the barrel.

In some embodiments, the methods may further comprise actuating a valve to provide fluid communication between the barrel and a target site of the patient's body, such that the negative gauge pressure draws fluid or material from the target site into the barrel. In some of such embodiments, actuating the valve may comprise manipulating the valve and gripping the syringe with only one hand.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

The invention claimed is:

1. A syringe assembly comprising:
    a barrel comprising:
        a seating region at a proximal end of the barrel; and
        an inner chamber extending between a distal end of the barrel and the seating region;
    a plunger comprising a plunger head coupled to a distal end of the plunger;
    a valve disposed adjacent the distal end of the barrel, wherein the valve is configured to selectively permit withdrawal of fluid into the barrel as the plunger is retracted within the barrel; and
    a locking mechanism operably coupled to the seating region of the barrel and the plunger, the locking mechanism comprising:
        a first cam surface configured to engage the plunger, wherein the first cam surface is substantially smooth; and
        a first outer surface configured to engage the seating region of the barrel, wherein the first cam surface is configured to transfer a rotational force from the plunger to a radial force on the seating region of the barrel via the first outer surface;
    wherein the locking mechanism is configured to lock the plunger to the barrel such that the plunger head is lockable at all points along the inner chamber of the barrel between the distal end of the barrel and the seating region of the barrel;
    wherein the locking mechanism restricts withdrawal and advancement of the plunger relative to the barrel when the plunger is locked to the barrel; and
    wherein the position of the locking mechanism relative to the barrel is fixed when the plunger is locked to the barrel.

2. The syringe assembly of claim 1, wherein the barrel and the locking mechanism are integrally formed.

3. The syringe assembly of claim 1, wherein the locking mechanism comprises one or more radially expanding components.

4. The syringe assembly of claim 1, wherein the locking mechanism comprises a partial ring having a variable radial thickness.

5. The syringe assembly of claim 1, wherein the valve is configured to maintain a vacuum in the barrel between the plunger and the valve.

6. The syringe assembly of claim 1, wherein the locking mechanism is at least partially disposed within the seating region of the barrel.

7. A syringe assembly comprising: a barrel comprising: a seating region at a proximal end of the barrel; a distal portion comprising an inlet/outlet port; and an inner chamber extending between the seating region and the distal portion, wherein an inner diameter of the seating region is greater than an inner diameter of the inner chamber, and wherein an inner diameter of the inner chamber is greater than an inner diameter of the distal portion; a plunger comprising: a longitudinal rib extending along a portion of a length of the plunger; and a plunger head coupled to a distal end of the plunger; a locking mechanism at least partially disposed within the seating region of the barrel, the locking mechanism comprising a cam surface engageable with the longitudinal rib; wherein the syringe assembly is transitionable between an unlocked configuration and a locked configuration when the plunger head is at all points along a length of the inner chamber of the barrel; wherein the plunger is longitudinally moveable within the inner chamber of the barrel when the syringe assembly is in the unlocked configuration; and wherein, when the syringe assembly is in the locked configuration, the longitudinal rib is engaged with the cam surface, thereby locking the plunger within the barrel such that both proximal and distal longitudinal movement of the plunger relative to the barrel is restricted.

8. The syringe assembly of claim 7, wherein the longitudinal rib applies a radial force to the cam surface when the syringe assembly is in the locked configuration.

9. The syringe assembly of claim 7, wherein the syringe assembly is configured to transition from the unlocked configuration to the locked configuration as a result of axial rotation of the plunger within the barrel.

10. The syringe assembly of claim 7, wherein the locking mechanism comprises a locking ring and the rib of the plunger corresponds to a locking surface of the locking ring.

11. The syringe assembly of claim 7, wherein the plunger comprises a plurality of longitudinal ribs and the locking mechanism comprises a plurality of cam surfaces, wherein the plurality of longitudinal ribs are engaged with the plurality of locking surfaces when the syringe assembly is in the locked configuration.

12. A syringe assembly, comprising:
- a barrel comprising:
  - a seating region at a proximal end of the barrel, the seating region comprising an aperture; and
  - an inlet/outlet port at a distal end of the barrel;
- a plunger; and
- a locking mechanism disposed within the seating region of the barrel, the locking mechanism comprising:
  - a first cam surface configured to engage the plunger; and
  - a first outer surface configured to engage the seating region of the barrel, wherein the first cam surface is configured to transfer a rotational force from the plunger to a radial force on the seating region,
  - wherein the aperture of the seating region is configured to allow an inner diameter of the seating region to deform outward as the radial force is applied on the seating region,
  - wherein the first cam surface is disposed within the seating region of the barrel such that longitudinal displacement of the plunger within the barrel does not displace the cam surface within the seating region of the barrel;
- and
- wherein the syringe assembly is configured to transition between an unlocked configuration that allows longitudinal movement of the plunger and a locked configuration that prevents longitudinal movement of the plunger when the plunger is at any position along a continuous portion of a length of the barrel.

13. The syringe assembly of claim 12, wherein the locking mechanism comprises a first partial ring that is configured to engage with the barrel to retain the first partial ring within the seating region of the barrel.

14. The syringe assembly of claim 13, further comprising a second partial ring disposed within the seating region of the barrel, operably connected to the plunger, and configured to restrict or allow longitudinal movement of the plunger based on the rotational position of the plunger.

15. A method of applying negative gauge pressure to a patient, the method comprising:
- obtaining the syringe assembly of claim 1 wherein the syringe assembly is configured to transition between an unlocked configuration and a locked configuration at any position along a continuous portion of a length of the barrel;
- withdrawing the plunger within the barrel to establish a negative gauge pressure within the barrel;
- axially rotating the plunger with respect to the barrel at a point along a length of the inner chamber of the barrel such that the first cam surface transitions from the unlocked configuration to the locked configuration to maintain negative gauge pressure; and
- actuating the valve to provide fluid communication between the barrel and a target site of the patient's body such that the negative gauge pressure draws fluid or material from the target site into the inner chamber of the barrel.

16. The method of claim 15, wherein actuating the valve comprises manipulating the valve and gripping the syringe assembly with only one hand.

* * * * *